(12) United States Patent
Enenkel

(10) Patent No.: US 8,466,271 B2
(45) Date of Patent: Jun. 18, 2013

(54) REGULATORY ELEMENTS

(75) Inventor: Barbara Enenkel, Warthausen (DE)

(73) Assignee: Boehringer Ingelheim Pharma GmbH & Co, KG, Ingelheim am Rhein (DE)

( * ) Notice: Subject to any disclaimer, the term of this patent is extended or adjusted under 35 U.S.C. 154(b) by 73 days.

(21) Appl. No.: 13/055,017

(22) PCT Filed: Jul. 22, 2009

(86) PCT No.: PCT/EP2009/059399
§ 371 (c)(1), (2), (4) Date: Mar. 15, 2011

(87) PCT Pub. No.: WO2010/010107
PCT Pub. Date: Jan. 28, 2010

(65) Prior Publication Data
US 2011/0312029 A1    Dec. 22, 2011

(30) Foreign Application Priority Data
Jul. 23, 2008 (EP) .................... 08161029

(51) Int. Cl.
*C07H 21/04* (2006.01)
*C12P 1/00* (2006.01)
*C12P 21/06* (2006.01)
*C12P 21/04* (2006.01)
*C12N 5/07* (2010.01)

(52) U.S. Cl.
USPC .......... 536/24.1; 435/41; 435/69.1; 435/70.1; 435/326; 435/328; 536/23.1; 536/23.4; 536/23.53

(58) Field of Classification Search
None
See application file for complete search history.

(56) References Cited

U.S. PATENT DOCUMENTS
2005/0175591 A1    8/2005 Stout et al.

FOREIGN PATENT DOCUMENTS
EP    0173552 A    3/1986

OTHER PUBLICATIONS

International Search Report and Written Opinion dated mailed Oct. 26, 2009 of corresponding PCT Application No: PCT/EP2009/059399.
Database EMBL: AL604045; Aug. 29, 2001 "Mouse DNA sequence from clone RP23-418O11 on chromosome 11 contains the 3' end of the Ernl gene for endoplasmic reticulum (ER) to nucleus signalling, the 3' end of the Ddx42 gene for DEAD (Asp-Glu-Ala-Asp) box polypeptide 42, the Cd79b gene for CD79B antigen, the Icam2 gene for intercellular adhesion" Database accession No. AL604045 sequences NT82216-82409.
Zarudnaya, Margarita I, et al. "Downstream elements of mammalian pre-mRNA polyadenylation signals: primary, secondary and higher-order structures" Nucleic Acids Research, Oxford University Presss, vol. 31, No. 5, Mar. 1, 2003, pp. 1375-1386.

*Primary Examiner* — Celine Qian
*Assistant Examiner* — Addison D Ault
(74) *Attorney, Agent, or Firm* — Michael P. Morris; Edouard G. Lebel

(57) ABSTRACT

The invention concerns novel regulatory elements as well as related vectors and cells. Furthermore, it relates to methods of improving expression of polypeptides from nucleic acids such as cloned genes and to the production of various polypeptides in host cells using said novel regulatory elements. Additionally, the invention relates to uses of said novel regulatory elements as insulators, in gene therapy or for improving host cell lines.

26 Claims, 7 Drawing Sheets

FIGURE 2

```
         GH for2
    ─────────────────────▶              Stop
  1 AGTGCCGTCG CTTTGTGGAA AGCAGCTGTG CCTTTTAGCA GCGGCGTCTC TGCTGGACTC
    TCACGGCAGC GAAACACCTT TCGTCGACAC GGAAAATCGT CGCCGCAGAG ACGACCTGAG 61 CCCAGCGCCC CCCTTTACCC TGGCAACTGC CCACCCCTAT GCTTTGCCCT AATAAAATGA
    GGGTCGCGGG GGGAAATGGG ACCGTTGACG GGTGGGGATA CGAAACGGGA TTATTTTACT 121 AGATGCATTG TATTGCTTGG CTAGATGTAT TTCTGTTGTG GGATGGAGGG TGGTGTCAAA
    TCTACGTAAC ATAACGAACC GATCTACATA AAGACAACAC CCTACCTCCC ACCACAGTTT 181 GAGTCCTAGA GGCCGACATG CCTGTGGGCT GCTGGAAGAA CAGCCCTGAC TTTGCCTGGA
    CTCAGGATCT CCGGCTGTAC GGACACCCGA CGACCTTCTT GTCGGGACTG AAACGGACCT 241 CCAAGTAGAG TCAACACATC ACTTCCCCTG TCTCGTGATG AGCCTGCTCC CACTCCAGAG
    GGTTCATCTC AGTTGTGTAG TGAAGGGGAC AGAGCACTAC TCGGACGAGG GTGAGGTCTC 301 TCAGAATCCC AGCTCTCTGG ACAGTCACAA GGCGGCAAGG TCCTATGTCA CCCCCATAAA
    AGTCTTAGGG TCGAGAGACC TGTCAGTGTT CCGCCGTTCC AGGATACAGT GGGGGTATTT

```
                                        1                                                    50
    C.griseus  (SEQ ID NO:8)     (1)  ----------CAGCGGCGTCTCTGCTGGACTCCCC-AGCGCCCCCCTTTACCC
    M.auratus  (S66299) 3´UTR    (1)  CAGGGCACTACGGTGTCTCTGCTGTACTCCCCCAGCGCCTCCCTTTGCCC
    M. musculus (Z46663) 3´UTR   (1)  --CCACTCACCAGTGTCTCTGCTGCACTCTCC-TGTGCCTCCCTGCCCCC
    R. norvegicus (V01239) 3´UTR (1)  --GCACACACTGGTGTCTCTGCGGCACTCCCCCGTTACCCCCCTGTACTC
    Bos taurus (J00008) 3´UTR    (1)  ---TTGCCAGCCATCTGTTGTTTGCCCCTCCCCCGTGCCTTCCTTGACCC
                                        51                                                  100
    C.griseus  (SEQ ID NO:8)    (43)  TGGCAACTGCCCACCCCTATGCTTTGCCCTAATAAAATGAAGA---TGCA
    M.auratus  (S66299) 3´UTR   (51)  TAGCAACTGCCCATCCCTATCGTTGCCCTAATAAAAT-AAGA---TGCA
    M. musculus (Z46663) 3´UTR  (48)  TGGCAACTGCC-ACCCCTCCGCTTTGTCCTAATAAAAT-AAGA---TGCA
    R. norvegicus (V01239) 3´UTR(49)  TGGCAACTGCC-ACCCCTACACTTTGTCCTAATAAAAT-AAGA---TGCA
    Bos taurus (J00008) 3´UTR   (48)  TGGAAGGTGCCACTCCCACTGTCCTTCCTAATAAAATGAGGAAATTGCA
                                        101                                                 150
    C.griseus  (SEQ ID NO:8)    (90)  TTGTATTGCTTGGCTAGATGTATTTCTGTTGTGGGATGGAGG-GTGGTGT
    M.auratus  (S66299) 3´UTR   (98)  TCATAAAAAAAAAAA
    M. musculus (Z46663) 3´UTR  (94)  TCATATCACCCGGCTAGAGGTCTTTCTGTTATGGGATGGAGCAGTTGTGT
    R. norvegicus (V01239) 3´UTR(95)  TCATATCACTCTGCTAGACATCTTTTTTTTTTTAAGGCGTCCGTTTTTT
    Bos taurus (J00008) 3´UTR   (98)  TCGCATTGTCTGAGTAGGTGTCATTCTATTCTGGGG-GGTGGGGTGGGGC
                                        151                                                 200
    C.griseus  (SEQ ID NO:8)   (139)  CAAAGAG--TCCTAGAGGCCGACATGCCTGTGGGCTGCTGGAAGAACAGC
    M.auratus  (S66299) 3´UTR  (112)
    M. musculus (Z46663) 3´UTR (144)  CAATCTTGTTCCTGGAAGCCTGCGAGAATCC-------
    R. norvegicus (V01239) 3´UTR(145) TTTTTAGATTTATTTATTTATTATAAG
    Bos taurus (J00008) 3´UTR  (147)  AGGACAG--CAAGGGGAGGATTGGGAAGACAATAGCAGGCATGCTGGG
                                        201                                                 250
    C.griseus  (SEQ ID NO:8)   (187)  CCTGACTTTGCCTGGACCAAGTAGAGTCAACACATCACTTCCCCTGTCTC
    M.auratus  (S66299) 3´UTR  (112)
    M. musculus (Z46663) 3´UTR (176)
    R. norvegicus (V01239) 3´UTR(172)
    Bos taurus (J00008) 3´UTR  (194)  GATGCGGTGGGCTCTATGGGTACCCAGGTGCTGAAGAATTGACCCGGTTC
                                        251                                                 300
    C.griseus  (SEQ ID NO:8)   (237)  GTGATGAGCCTGCTCCCACTCCAGAGTCAGAATCCCAGCTCTCTGGACAG
    M.auratus  (S66299) 3´UTR  (112)
    M. musculus (Z46663) 3´UTR (176)
    R. norvegicus (V01239) 3´UTR(172)
    Bos taurus (J00008) 3´UTR  (244)  CTCCTGGG
                                        301                              338
    C.griseus  (SEQ ID NO:8)   (287)  TCACAAGGCGGCAAGGTCCTATGTCACCCCCATAAAGT
    M.auratus  (S66299) 3´UTR  (112)
    M. musculus (Z46663) 3´UTR (176)
    R. norvegicus (V01239) 3´UTR(172)
    Bos taurus (J00008) 3´UTR  (252)
```

FIGURE 4

```
                                        Stop      50
HGH 362 nt (SEQ ID NO:7)    (1) AGTGCCGTCGCTTTGTGGAAAGCAGCTGTGCCTTTTAGCAGCGGCGTCTC
HGH 324 nt (SEQ ID NO:8)    (1) ---------------------------------------CAGCGGCGTCTC
HGH 189 nt (SEQ ID NO:9)    (1) ---------------------------------------CAGCGGCGTCTC
HGH 113 nt (SEQ ID NO:10)   (1) ---------------------------------------CAGCGGCGTCTC
                                 51                                              100
HGH 362 nt (SEQ ID NO:7)   (51) TGCTGGACTCCCCAGCGCCCCCCTTTACCCTGGCAACTGCCCACCCCTAT
HGH 324 nt (SEQ ID NO:8)   (13) TGCTGGACTCCCCAGCGCCCCCCTTTACCCTGGCAACTGCCCACCCCTAT
HGH 189 nt (SEQ ID NO:9)   (13) TGCTGGACTCCCCAGCGCCCCCCTTTACCCTGGCAACTGCCCACCCCTAT
HGH 113 nt (SEQ ID NO:10)  (13) TGCTGGACTCCCCAGCGCCCCCCTTTACCCTGGCAACTGCCCACCCCTAT
                                101                                              150
HGH 362 nt (SEQ ID NO:7)  (101) GCTTTGCCCTAATAAAATGAAGATGCATTGTATTGCTTGGCTAGATGTAT
HGH 324 nt (SEQ ID NO:8)   (63) GCTTTGCCCTAATAAAATGAAGATGCATTGTATTGCTTGGCTAGATGTAT
HGH 189 nt (SEQ ID NO:9)   (63) GCTTTGCCCTAATAAAATGAAGATGCATTGTATTGCTTGGCTAGATGTAT
HGH 113 nt (SEQ ID NO:10)  (63) GCTTTGCCCTAATAAAATGAAGATGCATTGTATTGCTTGGCTAGATGTAT
                                151                                              200
HGH 362 nt (SEQ ID NO:7)  (151) TTCTGTTGTGGGATGGAGGGTGGTGTCAAAGAGTCCTAGAGGCCGACATG
HGH 324 nt (SEQ ID NO:8)  (113) TTCTGTTGTGGGATGGAGGGTGGTGTCAAAGAGTCCTAGAGGCCGACATG
HGH 189 nt (SEQ ID NO:9)  (113) TTCTGTTGTGGGATGGAGGGTGGTGTCAAAGAGTCCTAGAGGCCGACATG
HGH 113 nt (SEQ ID NO:10) (113) T-------------------------------------------------
                                201                                              250
HGH 362 nt (SEQ ID NO:7)  (201) CCTGTGGGCTGCTGGAAGAACAGCCCTGACTTTGCCTGGACCAAGTAGAG
HGH 324 nt (SEQ ID NO:8)  (163) CCTGTGGGCTGCTGGAAGAACAGCCCTGACTTTGCCTGGACCAAGTAGAG
HGH 189 nt (SEQ ID NO:9)  (163) CCTGTGGGCTGCTGGAAGAACAGCCCT-----------------------
HGH 113 nt (SEQ ID NO:10) (114) --------------------------------------------------
                                251                                              300
HGH 362 nt (SEQ ID NO:7)  (251) TCAACACATCACTTCCCCTGTCTCGTGATGAGCCTGCTCCCACTCCAGAG
HGH 324 nt (SEQ ID NO:8)  (213) TCAACACATCACTTCCCCTGTCTCGTGATGAGCCTGCTCCCACTCCAGAG
HGH 189 nt (SEQ ID NO:9)  (190) --------------------------------------------------
HGH 113 nt (SEQ ID NO:10) (114) --------------------------------------------------
                                301                                              350
HGH 362 nt (SEQ ID NO:7)  (301) TCAGAATCCCAGCTCTCTGGACAGTCACAAGGCGGCAAGGTCCTATGTCA
HGH 324 nt (SEQ ID NO:8)  (263) TCAGAATCCCAGCTCTCTGGACAGTCACAAGGCGGCAAGGTCCTATGTCA
HGH 189 nt (SEQ ID NO:9)  (190) --------------------------------------------------
HGH 113 nt (SEQ ID NO:10) (114) --------------------------------------------------
                                351       362
HGH 362 nt (SEQ ID NO:7)  (351) CCCCCATAAAGT
HGH 324 nt (SEQ ID NO:8)  (313) CCCCCATAAAGT
HGH 189 nt (SEQ ID NO:9)  (190) ------------
HGH 113 nt (SEQ ID NO:10) (114) ------------
```

FIGURE 6

| Vector | Termination Sequence | Transient Transfection #1 (n=2) | Transient Transfection #2 (n=2) |
|---|---|---|---|
| pJR106 | SV40 late (SEQ ID NO: 11) | 193 ng/mL sICAM | 207 ng/mL sICAM |
| pJR110 | BGH (SEQ ID NO: 12) | 222 ng/mL sICAM | 234 ng/mL sICAM |
| pJR131 | HGH (SEQ ID NO: 8) | 269 ng/mL sICAM | 257 ng/mL sICAM |

FIGURE 7

| Vector combination | Termination Sequence | Transient Transfection (n=6) |
|---|---|---|
| pBID-B/IgG4 + pBIN-B/kappa | BGH (SEQ ID NO: 12) | 40 ± 6 ng/mL IgG4 |
| pBID/IgG4 + pBIN/kappa | HGH (SEQ ID NO: 8) | 54 ± 8 ng/mL IgG4 |

FIGURE 8

| Vector | HGH Sequence (3´UTR) | Transient Transfection #1 (n=2) | Transient Transfection #2 (n=2) |
|---|---|---|---|
| pJR131 | bp 1 – 324 (SEQ ID NO: 8) | 111 ng/mL sICAM | 108 ng/mL sICAM |
| pJR134 | bp 1- 189 (SEQ ID NO: 9) | 98 ng/mL sICAM | 83 ng/mL sICAM |
| pJR135 | bp 1- 113 (SEQ ID NO: 10) | 25 ng/mL sICAM | 25 ng/mL sICAM |

FIGURE 9

| Product | Cell Clone/ Cell Pool | Specific Productivity (pg/cell/day) | Titer in Fed Batch Process |
|---|---|---|---|
| IgG1 (1) | cell clone | 23 | 6.3 g/L (40 L bioreactor) |
| IgG1 (2) | cell pool (800 nM MTX) | 32 | 2.5 g/L (shake flask) |
| IgG2 | cell clone | 10 | 2.1 g/L (2 L bioreactor) |
| IgG4 | cell pool (800 nM MTX) | 44 | 2.1 g/L (shake flask) |
| Fc fusion protein (IgG1) | cell pool (800 nM MTX) | 45 | 3.9 g/L (shake flask) |
| Fc fusion protein (IgG2) | cell pool (800 nM MTX) | 34 | 3.4 g/L (shake flask) |

REGULATORY ELEMENTS

BACKGROUND OF THE INVENTION

1. Technical Field

The invention concerns the field of cell culture technology. It concerns novel regulatory elements as well as a method to improve expression of polypeptides from nucleic acids such as cloned genes and the production of various polypeptides in eukaryotic host cell using said novel regulatory elements.

2. Background

The market for biopharmaceuticals for use in human therapy continues to grow at a high rate with over 900 biopharmaceuticals being evaluated in clinical studies and estimated sales of 50 billions in 2010. Currently, an increasing number of biopharmaceuticals is produced from mammalian cells due to their ability to correctly process and modify human proteins. Therefore the recombinant proteins are compatible with humans both functionally and pharmacokinetically. A shortcoming compared to prokaryotic expression systems is often the significantly lower protein expression level. Successful and high yield production of biopharmaceuticals from mammalian cells is thus crucial and is governed by various factors including host cell line, expression system, cell growth and productivity, culture and feed media, production and purification process, protein structure and sequence, protein stability and formulation.

Expression of the recombinant protein requires an expression vector encoding the desired gene of interest. Several methods have been employed to optimize expression vectors for efficient protein production. Gene expression is regulated on transcriptional and translational levels. Hence many methods pertain to the identification and optimization of strong promoters and enhancers to improve the efficiency with which protein encoding genes are transcribed. Examples of these are the CMV immediate early promoter and enhancer, SV40 promoter and enhancer, elongation factor (EF) promoter, Polyoma enhancer, and chicken [beta]-actin promoter. Likewise, strong polyadenylation signal sequences that stabilize mRNAs and enhance transcription termination are also used to augment the protein expression from genes encoded by the expression vectors. Among the methods to improve the efficiency with which the resultant mRNA is translated are the use of translation initiation sites (AUG), optimal ribosome binding sites such as the Kozak sequence (GCCGCCAC-CAUGG; AUG constitutes the start codon) or internal ribosome entry sites (IRES).

One of the methods employed to optimize expression vectors in order to obtain higher levels of recombinant gene expression in eukaryotic cells pertains to the use and selection of polyadenylation signals. A variety of polyadenylation signals are used in vectors for the expression of recombinant proteins. The most commonly used include for example polyadenylation signals from bovine growth hormone (BGH) (U.S. Pat. No. 5,122,458), simian virus 40 late and early region, rabbit beta-globin, mouse or human immunoglobulins, polyoma virus late region.

In eukaryotic messenger RNA (mRNA) the 3' untranslated region (3'UTR) is an important regulatory element. In many instances it dictates mRNA stability and it can also regulate translation efficiency. Polyadenylation signals are nucleotide sequences within the 3'UTR that direct binding of a polyadenylation protein complex to an AAUAAA sequence within the signal sequence. The complex contains an endonuclease that cuts the mRNA about 14 to 30 nucleotides downstream of the AAUAAA sequence and a polymerase that incorporates post-transcriptionally a string of approximately 100 to 200 adenine nucleotides (polyA tail) to the cleaved 3' end. The polyA tail is believed to influence many aspects of mRNA metabolism, including stability, translational efficiency, and transport from the nucleus to the cytoplasm. Typically, the polyadenylation signal consists of two recognition elements flanking the cleavage and polyadenylation site: a highly conserved AAUAAA sequence approximately 14 to 30 nucleotides upstream of the cleavage site and a poorly conserved G/U- or U-rich region approximately 20 to 50 nucleotides downstream of the AAUAAA sequence. Cleavage between these two elements is usually on the 3' side of an A residue. In vivo, the efficiency with which different polyadenylation sites are processed varies considerably. The assembly speed of the polyadenylation protein complex is a multistep process and correlates with the strength of the polyadenylation signal sequence. For example, due to faster assembly rate cleavage in the strong SV40 late polyadenylation signal occurs more rapidly than in the weaker SV40 early polyadenylation signal (Chao et al., Molecular and Cellular Biology, Vol. 19 (8), 5588-5600, 1999).

There is the need to identify alternative strong or even very strong polyadenylation signals to accelerate the generation of high producer cell lines for the production of recombinant proteins. The use of strong or even very strong polyadenylation signals enhances transcriptional termination which in turn results in increased production, stability, nuclear export and/or translation of vector encoded mRNA. This should lead to higher mRNA levels and hence result in higher productivity of producer cells.

SUMMARY OF THE INVENTION

Solution

Here we describe a new polyadenylation signal isolated from the growth hormone of the Chinese hamster (*Cricetus griseus*). Surprisingly, it has been found that this newly identified polyadenylation signal, named HGH, outperforms the strong polyadenylation signals BGH and SV40 late. When using vectors comprising HGH as polyadenylation signal sequence protein titers in transient transfections of CHO-DG44 cells were increased up to 35% compared to cells comprising BGH. In stable cells high specific productivities up to 45 pg/cell/day and titers in fed batch processes up to 6.3 g/L were obtained.

One embodiment of the present invention is a polynucleotide sequence comprising at least one HGH polyadenylation signal and at least one heterologous nucleotide sequence encoding a product of interest. The HGH polyadenylation signal is downstream and operably linked to the heterologous nucleotide sequence(s). Another embodiment of the present invention is a novel vector comprising at least one heterologous nucleotide sequence encoding a product of interest and at least one HGH polyadenylation signal. The HGH polyadenylation signal is downstream and operably linked to the heterologous nucleotide sequence(s). A further embodiment of the present invention is a novel vector or polynucleotide sequence comprising at least one HGH polyadenylation signal operably linked to an upstream multiple cloning site which allows the cloning of the gene of interest via recognition sequences for restriction endonucleases. Yet another embodiment of the present invention is a eukaryotic cell, preferably a mammalian cell, comprising the HGH polyadenylation signal. Yet a further embodiment of the present invention is a method for producing a product of interest comprising culturing eukaryotic cells, preferably mammalian cells transfected with vectors or polynucleotide sequences comprising the HGH polyadenylation signal. In a preferred embodiment the product of interest is a polypeptide and the desired polypeptide is recovered from the culture medium.

The data of the present invention show the impact of the HGH polyadenylation signal sequence on the transient expression of sICAM (FIG. 6). Surprisingly, the highest sICAM expression is obtained with the polyadenylation signal sequence derived from the growth hormone gene of hamster. The titer is increased up to 21% (transfection series #1) compared to cells transfected with the vector pJR110 containing the BGH polyadenylation signal and increased up to 40% (transfection series #1) compared to cells transfected with the vector pJR106 containing the SV40 late polyadenylation signal.

The data of the present invention furthermore show the impact of HGH polyadenylation signal on the transient expression of an IgG4 antibody. Surprisingly, titers obtained with the HGH polyadenylation signal sequence are on average 35% higher than for the BGH polyadenylation signal (FIG. 7).

The data of the present invention additionally show a test of different HGH variants (FIG. 8). The shortest HGH sequence of 113 bp contained in the expression vector pJR135 leads to a up to 78% reduced sICAM expression in comparison to the HGH sequence of 324 bp contained in the expression vector pJR131. Whereas the HGH sequence of 189 bp contained in the expression vector pJR134 results in a very good sICAM expression comparable to the expression level achieved with BGH (FIG. 7). The best expression result is achieved with the HGH sequence of 324 bp contained in the expression vector pJR131 (FIG. 8), which is much better (35%) than the expression achieved with BGH polyadenylation signal (FIG. 7).

This shows that between the HGH region of by 190 to 324 of SEQ ID NO:8 sequences are located which contribute to an efficient expression of a gene of interest.

The data of the present invention furthermore show stable expression of proteins at high levels using the HGH polyadenylation signal. Cell pools and cell clones with specific productivities in the range of 10-45 pg/cell/day and titers in fed batch processes of up to 6.3 g/L are obtained (FIG. 9).

The invention relates to a polyadenylation signal comprising a nucleic acid comprising a sequence at least 75% identical to SEQ ID NO:9. The invention further relates to a polyadenylation signal comprising a nucleic acid comprising a sequence having at least 75% identity to SEQ ID NO:9. The invention furthermore relates to a polyadenylation signal comprising a nucleic acid comprising a sequence with at least 75% identity to SEQ ID NO:9. The invention specifically relates to a polyadenylation signal comprising a nucleic acid consisting essentially of a sequence at least 75% identical to SEQ ID NO:9.

The invention preferably relates to a polyadenylation signal comprising a nucleic acid consisting of a sequence at least 75% identical to SEQ ID NO:9. The invention furthermore relates to a polyadenylation signal comprising a nucleic acid comprising SEQ ID NO:9.

In a specific embodiment the invention relates to a polyadenylation signal comprising a nucleic acid comprising a sequence at least 75% identical to SEQ ID NO:8. The invention specifically relates to a polyadenylation signal comprising a nucleic acid consisting essentially of a sequence at least 75% identical to SEQ ID NO:8. The invention preferably relates to a polyadenylation signal comprising a nucleic acid consisting of a sequence at least 75% identical to SEQ ID NO:8. The invention furthermore relates to a polyadenylation signal comprising a nucleic acid comprising SEQ ID NO:8.

In a further embodiment of the present invention the polyadenylation signal comprises a sequence at least 80%, 85%, 90%, 95% or 98% identical to SEQ ID NO:9 or SEQ ID NO:8. In a specific embodiment the invention relates to a polyadenylation signal comprising a nucleic acid comprising a sequence at least 85% identical to SEQ ID NO:9. In another specific embodiment the invention relates to a polyadenylation signal comprising a nucleic acid comprising a sequence at least 95% identical to SEQ ID NO:9. In a specific embodiment the invention relates to a polyadenylation signal comprising a nucleic acid comprising a sequence at least 85% identical to SEQ ID NO:8. In another specific embodiment the invention relates to a polyadenylation signal comprising a nucleic acid comprising a sequence at least 95% identical to SEQ ID NO:8.

The invention relates to a nucleic acid the sequence of which comprises SEQ ID NO:9. Preferably, the invention relates to a nucleic acid the sequence of which consists essentially of SEQ ID NO:9. More preferably, the invention relates to a nucleic acid the sequence of which consists of SEQ ID NO:9.

The invention relates to a nucleic acid the sequence of which comprises SEQ ID NO:8. Preferably, the invention relates to a nucleic acid the sequence of which consists essentially of SEQ ID NO:8. More preferably, the invention relates to a nucleic acid the sequence of which consists of SEQ ID NO:8.

In a preferred embodiment said polyadenylation signal is isolated. In a preferred embodiment the invention relates to an isolated polyadenylation signal comprising a nucleic acid comprising a sequence at least 75% identical to SEQ ID NO:9. In another preferred embodiment the invention relates to an isolated polyadenylation signal comprising a nucleic acid comprising a sequence at least 95% identical to SEQ ID NO:9. In still another preferred embodiment the invention relates to an isolated polyadenylation signal comprising a nucleic acid comprising SEQ ID NO:9. In a further preferred embodiment the invention relates to an isolated polyadenylation signal comprising a nucleic acid comprising a sequence at least 75% identical to SEQ ID NO:8. In another preferred embodiment the invention relates to an isolated polyadenylation signal comprising a nucleic acid comprising a sequence at least 95% identical to SEQ ID NO:8. In still another preferred embodiment the invention relates to an isolated polyadenylation signal comprising a nucleic acid comprising SEQ ID NO:8.

Preferably, the invention relates to an isolated nucleic acid the sequence of which comprises SEQ ID NO:9. More preferably, the invention relates to an isolated nucleic acid the sequence of which comprises SEQ ID NO:8.

In a preferred embodiment said polyadenylation signal is operably linked to a heterologous coding sequence. In a specifically preferred embodiment said polyadenylation signal is characterized by that the titers/expression levels obtained with the said polyadenylation signal are at least 10%, preferably 20% and most preferably 30% higher than those obtained for the BGH polyadenylation signal. In a most preferred embodiment they are at least and/or on average 35% higher than those obtained for the BGH polyadenylation signal.

The invention specifically relates to a nucleic acid the sequence of which comprises SEQ ID NO:9 operably linked to a heterologous coding sequence. Alternatively, the sequence of which consists essentially of SEQ ID NO:9 operably linked to a heterologous coding sequence. Preferably, the sequence of which consists of SEQ ID NO:9 operably linked to a heterologous coding sequence.

The invention furthermore relates to a nucleic acid the sequence of which comprises SEQ ID NO:8 operably linked to a heterologous coding sequence. Alternatively, the sequence of which consists essentially of SEQ ID NO:8 operably linked to a heterologous coding sequence. Preferably, the sequence of which consists of SEQ ID NO:8 operably linked to a heterologous coding sequence.

A nucleic acid the sequence of which comprises SEQ ID NO:9 or 8 and has terminator function. Preferably said nucleic acid has terminator function and is operably linked to a heterologous coding sequence.

The invention furthermore relates to a vector or polynucleotide sequence which comprises any one of the polyadenylation signals or nucleic acid sequences as described above. In a specific embodiment said polyadenylation signals or nucleic acid sequences are operably linked to an expression unit/expression cassette. In another embodiment of the invention the vector comprises the selection and/or amplification marker dihydrofolate reductase (DHFR), glutamine synthetase or neomycin phosphatase (neo). In a preferred embodiment of the present invention the vector or polynucleotide sequence comprises a heterologous gene of interest encoding for a heterologous product of interest. Preferably said product is a polypeptide. Preferably said polypeptide is an antibody, antibody fragment or fusion protein.

The invention additionally relates to a cell comprising any one of the vectors or polynucleotide sequences as described above. Preferably, the cell comprises any one of the polyadenylation signals or nucleic acid sequences as described above operably linked to a transcription unit encoding a product of interest. Preferably said product of interest is a nucleotide/nucleic acid of interest. In another embodiment of the cell said product of interest is a polypeptide of interest encoded by a gene of interest. Preferably said polypeptide is an antibody, antibody fragment or fusion protein.

In a specific embodiment said cell is a eukaryotic cell, a mammalian cell, a hamster cell or a murine cell. Preferably said cell is a hamster cell. More preferably, said cell is Chinese hamster ovary (CHO) cell. Most preferably said cell is a CHO DG44, CHO-K1 or DUKX-B11 cell. In another preferred embodiment said cell is a NSO cell. In a preferred embodiment said cells as described are cultured cells. Preferably, said cells are cultured in serum-free medium. Preferably said cells are grown in suspension culture. In another preferred embodiment of the present invention the cell is characterized by that the titers/expression levels obtained with said polyadenylation signal or nucleic acid sequence are at least 10%, preferably 20% and most preferably 30% higher than those obtained for the BGH polyadenylation signal. In a most preferred embodiment they are at least and/or on average 35% higher than those obtained for the BGH polyadenylation signal. Preferably, said cell has 35% higher expression levels.

The invention additionally relates to a method of making a polypeptide of interest encoded by a gene of interest, the method comprising:
(a) Providing a host cell comprising a vector or polynucleotide sequence as described above or providing a cell as described above,
(b) Cultivating said cells, under conditions which allow the proliferation of the cells and the expression of the gene of interest,
(c) Harvesting the polypeptide of interest and
(d) Purifying the polypeptide of interest.

In a specific embodiment of said method the cell is a eukaryotic cell, a mammalian cell, a hamster cell or a murine cell. Preferably said cell is a CHO cell, most preferably a CHO DG44, CHO-K1 or DUKX-B11 cell. Furthermore preferred is a NSO cell.

In a preferred embodiment of said method the polypeptide of interest is a recombinant protein, preferably a secreted polypeptide, more preferably a therapeutic protein. Most preferably the polypeptide of interest is an antibody, such as a monoclonal, polyclonal, multispecific or single chain antibody, or a fragment thereof, e.g. Fab, Fab', F(ab')2, Fc and Fc'-fragments, heavy and light immunoglobulin chains and their constant, variable or hypervariable region as well as Fv- and Fd-fragments. In another preferred embodiment of said method the polypeptide of interest is a fusion protein or a scaffold protein.

The invention further relates to a use of the cell as described above for the manufacturing of proteins.

The invention furthermore relates to a use of any one of the polyadenylation signals or nucleic acids as described above for the use as an insulator.

Additionally, the invention relates to a use of any one of the polyadenylation signals or nucleic acids as described above for the generation of improved host cell lines.

The invention specifically relates to a use of any one of the polyadenylation signals or nucleic acids as described above for the use in gene therapy.

The invention further relates to a kit comprising any one of the polyadenylation signals or nucleic acids as described above, a vector, a cell and a cell culture medium for cultivation of said cell.

DESCRIPTION OF THE FIGURES

FIG. 1 schematically shows the expression vector designs used for the transfection of CHO-DG44 cells. "P/E" means a composite unit that contains both CMV enhancer and promoter element, "P" a promoter element and "T" a termination signal for transcription, which is required for polyadenylation of transcribed messenger RNA. The polyadenylation signals "BGH", "SV40L" and "HGH" are termination signals for transcription derived from the 3' untranslated region of bovine growth hormone (SEQ ID NO:12), the SV40 late gene region (SEQ ID NO:11) and 3' untranslated region of Chinese hamster growth hormone (SEQ ID NO:8), respectively. These polyadenylation signals are flanked by restriction enzyme sites for "SfiI" and "XbaI". The position and direction of transcription initiation within each transcription unit is indicated by an arrow. For cloning of the gene of interest a sequence region with multiple cutting sites for restriction endonucleases (multiple cloning sites—"mcs") is inserted after the promoter/enhancer element. The amplifiable selectable marker dihydrofolate reductase is abbreviated to "dhfr" and the selectable marker neomycin phosphotransferase is abbreviated to "npt".

FIG. 2: Isolated Growth Hormone Gene Region of *Cricetus griseus*

FIG. 2 shows the nucleotide sequence of the growth hormone gene region which was amplified from genomic CHO-DG44 (Chinese Hamster Ovary cell line; *Cricetus griseus*) DNA using nested PCR with in total 362 bp (SEQ ID NO:7). The arrow indicates the direction, length and position of the gene specific primer GH for2 used in the amplification reaction, the primer sequence itself is highlighted in italics (SEQ ID NO:2). The stop codon TAG of the growth hormone gene sequence is highlighted by underlined bold letters and is followed by 324 bp of the 3' untranslated region.

FIG. 3: Alignment of 3' Untranslated Regions of Growth Hormone Genes

In this alignment the isolated 3' untranslated region of the Cricetus griseus growth hormone (SEQ ID NO:8) is compared to the 3' untranslated growth hormone region of the syrian hamster Mesocricetus auratus (Genbank S66299), Mus musculus (Genbank Z46663), Rattus norvegicus (Genbank V01239) and Bos taurus (Genbank J00008). Shading indicates nucleotides differing from the C. griseus sequence.

FIG. 4: HGH Deletion Derivates of 3' Untranslated Region of Cricetus griseus Growth Hormone In this alignment the deletion derivates of the 362 nucleotide Cricetus griseus growth hormone (HGH) sequence (SEQ ID NO:7) containing just the 3' untranslated region are shown. All derivates have an identical 5' end and differ in their 3' ending. The longest derivate with SEQ ID NO:8 consists of 324 nucleotides. SEQ ID NO:9 consists of 189 nucleotides and SEQ ID NO:10 of just 113 nucleotides. The stop codon TAG of the growth hormone gene sequence is highlighted by underlined bold letters and the potential binding site for the polyadenylation protein complex AATAAA is highlighted in italics.

Figure 5:
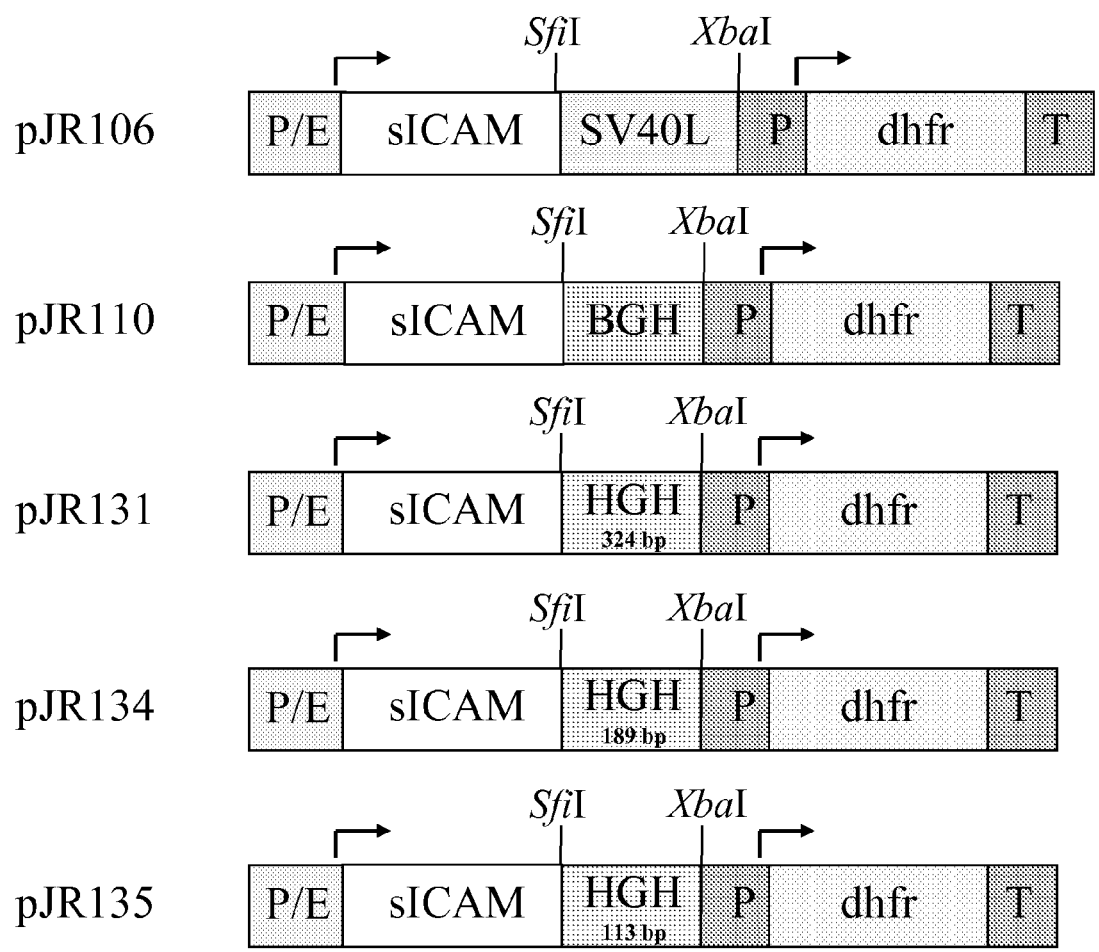

FIG. 5: Recombinant Expression Vectors for Evaluation of HGH Performance

All recombinant expression vectors encode the gene of interest "sICAM" under the control of the CMV enhancer and promoter element ("PIE"). sICAM transcription is either terminated by the 3' untranslated region of bovine growth hormone "BGH" (SEQ ID NO:12), the SV40 late gene region "SV40L" (SEQ ID NO:11) or the 3' untranslated region of Chinese hamster growth hormone "HGH" (SEQ ID NO:8, SEQ ID NO:9, SEQ ID NO:10). The size of the latter in basepairs is indicated. These polyadenylation signals are flanked by restriction enzyme sites for "SfiI" and "XbaI". "P" indicates a promoter element and "T" a termination signal for transcription. The position and direction of transcription initiation within each transcription unit is indicated by an arrow. The amplifiable selectable marker dihydrofolate reductase is abbreviated to "dhfr".

FIG. 6: Evaluation of HGH Performance in Transient Transfections

In two independent series CHO-DG44 cells are transfected with expression vectors pJR106, pJR110 and pJR131 all of which encode sICAM under the CMV enhancer/promoter. For termination of transcription either the SV40 late polyadenylation signal (SEQ ID NO:11), the 3' untranslated region of bovine growth hormone BGH (SEQ ID NO:12) or the 3' untranslated region of Chinese hamster growth hormone HGH (SEQ ID NO:8) are used. After a period of 48 hours the sICAM titers in the supernatants are determined using ELISA. To correct for transfection efficiency cells are co-transfected with the plasmid pCMV-SEAP and the SEAP activity is measured. Using HGH as polyadenylation signal the titer is increased up to 21% compared to termination with BGH and up to 40% compared to termination with SV40 late.

FIG. 7: Evaluation of HGH Performance in Transient Expression of an IgG4/Kappa Antibody CHO-DG44 cells are co-transfected with the vector combination pBID/IgG4 and pBIN/kappa (n=6) in which the transcription of the heavy (IgG4) and light chain (kappa) of the antibody is terminated by the 324 bp 3' untranslated region of the Chinese hamster growth hormone HGH (SEQ ID NO:8). As a control CHO-DG44 cells are co-transfected with the vector combination pBID-B/IgG4 and pBIN-B/kappa (n=6) which contain the BGH polyadenylation signal (SEQ ID NO:12). Aside of the different polyadenylation sequences the genetic setup of the various vectors are identical. After a period of 48 hours the antibody titers in the supernatants are determined using ELISA. To correct for transfection efficiency cells are co-transfected with the plasmid pCMV-SEAP and the SEAP activity is measured. Using HGH as polyadenylation signal titers are on average 35% higher than for BGH polyadenylation signals.

FIG. 8: Test of Different HGH Deletion Variants in Transient Transfections

In two independent series CHO-DG44 cells are transfected with expression vectors pJR131, pJR134 and pJR135 all of which encode sICAM under the CMV enhancer/promoter. For termination of transcription either 324 bp (SEQ ID NO:8), 189 bp (SEQ ID NO:9) or 113 bp (SEQ ID NO:10) of the 3' untranslated region of Chinese hamster growth hormone HGH are used. All variants have an identical 5' end but differ in their 3' end. Aside of the different polyadenylation sequences the genetic setup of the various vectors are identical. 48 hours post transfections the sICAM titers in the supernatants are determined using ELISA. To correct for transfection efficiency cells are co-transfected with the plasmid pCMV-SEAP and the SEAP activity is measured. Compared to cells transfected with vectors containing the 324 bp HGH sequence cells transfected with vectors containing the 189 bp and the 113 bp HGH deletion variants show a reduction in sICAM expression levels of 23% and 78%, respectively.

FIG. 9: High Level Protein Expression in Stable Transfected Cells Using HGH

In FIG. 9 the specific productivities and titers of stably transfected CHO-DG44 cell clone or cell pools expressing IgG1, IgG2 and IgG4 antibodies or IgG1 and IgG2 Fc fusion proteins in fed-batch processes performed in bioreactors or shake flasks are summarized. Specific productivities are in the range of 10-45 pg/cell/day and titers are in the range of 2.1-6.3 g/L. The genetic setup of the vectors used for expression of the various proteins is identical. All contain the 324 bp 3' untranslated region of Chinese hamster growth hormone (SEQ ID NO:8) as polyadenylation signal to terminate the transcription of the gene of interest. 2 days post transfection stable cell pools are selected using a DHFR- and NPT-based selection followed by 2 successive DHFR-mediated gene amplification steps by addition of 100 nM and 800 nM MTX to the culture medium. Single cell clones are obtained either by dilution cloning or a FACS-based deposition of single cells into wells of a 96 well plate.

DETAILED DESCRIPTION OF THE INVENTION

The general embodiments "comprising" or "comprised" encompass the more specific embodiment "consisting of". Furthermore, singular and plural forms are not used in a limiting way.

The present invention provides novel regulatory elements and methods of preparing and selecting mammalian cell lines which allow a high expression of heterologous gene products, preferably biopharmaceutically relevant polypeptides or proteins. The processes according to the invention are based primarily on the use of novel polyadenylation signals isolated from the growth hormone of the Chinese hamster (Cricetus griseus). Surprisingly, it has been found that this newly identified polyadenylation signal, named HGH (SEQ ID No:8), outperforms the strong polyadenylation signals BGH and SV40 late leading to higher productivity of producer cells.

Terms used in the course of this present invention have the following meaning.

The terms "polyadenylation signal", "polyadenylation site", "polyA signal", "polyA site" or "termination signal" or "terminator" refer to nucleotide sequences within the 3'UTR that direct binding of a polyadenylation protein complex to an AAUAAA sequence within the signal sequence. The complex contains an endonuclease that cuts the mRNA about 14 to 30 nucleotides downstream of the AAUAAA sequence and a polymerase that incorporates post-transcriptionally a string of approximately 100 to 200 adenine nucleotides (polyA tail) to the cleaved 3' end. The polyA tail is believed to influence many aspects of mRNA metabolism, including stability, translational efficiency, and transport from the nucleus to the cytoplasm. Typically, the polyadenylation signal consists of two recognition elements flanking the cleavage and polyadenylation site: a highly conserved AAUAAA sequence approximately 14 to 30 nucleotides upstream of the cleavage site and a poorly conserved G/U- or U-rich region approximately 20 to 50 nucleotides downstream of the AAUAAA sequence. Cleavage between these two elements is usually on the 3' side of an A residue. Various polyadenylation signals are known such as tk polyA (Cole et al., Mol. Cell. Biol., 5, 2104-2113, 1985), SV40 late (Schek et al., Mol. Cell. Biol. 12, 5386-5393, 1992) and early polyA or BGH polyA (described for example in U.S. Pat. No. 5,122,458).

While in the polyadenylation signal the AAUAAA sequence described above is preferred, it might be substituted with other hexanucleotide sequences with homology to AAUAAA as long as they are capable of signaling polyadenylation of mRNAs. Examples of homologous hexanucleotide sequences include AAAAAA, AUUAAA, AAUAUA, AAUAAU, UAUAAA, AAUUAA, AAUAAG, AGUAAA, GAUAAA, AAUGAA, AAUAGA, AAGAAA, ACUAAA, CAUAAA, AAUCAA, AACAAA, AAUCAA, and AAUAAC. Therefore, in one embodiment the HGH polyadenylation signal comprises a hexanucleotide sequence selected from the group consisting of AAAAAA, AUUAAA, AAUAUA, AAUAAU, UAUAAA, AAUUAA, AAUAAG, AGUAAA, GAUAAA, AAUGAA, AAUAGA, AAGAAA, ACUAAA, CAUAAA, AAUCAA, AACAAA, AAUCAA, and AAUAAC rather than the present AAUAAA as long as these hexanucleotides are capable of signaling polyadenylation of mRNAs.

Polyadenylation signals might be also used as "insulators" or "insulating sequences". Insulating sequences are segments of DNA that block interactions or interference of neighboring gene sequences. For example, insulators can reduce the transcriptional read through from a promoter of a neighboring gene or spurious promoters in adjacent nucleotide sequences. Or they block the interaction of an enhancer on one side of the insulating sequence with a promoter of a neighboring gene on the other side of the insulating sequence. The defining characteristic of an insulating sequence within the meaning of the present invention is its ability to insulate or protect a defined transcription unit which is operably linked to a regulatory element from the influence of an upstream or downstream interfering genetic element. For this purpose the insulating sequence is placed between the (potential) interfering genetic sequence and the regulatory sequence of the transcription unit to be insulated. The insulating sequence might be placed on either or both sides of the transcription unit in one or more copies. In a preferred embodiment of the present invention the insulating sequence is a polyadenylation signal. In a preferred embodiment of this invention the polyadenylation sequence is the HGH polyadenylation sequence.

It is also possible to use functional derivatives of the HGH polyadenylation sequence such as subfragments or subsequences as well as functional mutants/variants of the complete sequence or subfragments thereof which have been modified, for example, by substitution, insertion, addition and/or deletion. Corresponding subfragments or subsequences, mutants or variants are hereinafter also referred to as "modified terminators" or "derivative".

A "modified terminator" or "derivative" is a functional derivative of SEQ ID NO:8, which includes subfragments or subsequences and functional mutants/variants, and preferably leads to expression levels of a product of interest comparable to expression levels obtained with the nucleotide sequence given in SEQ ID NO:8. A modified terminator proves to be useful for the purposes of the invention if the expression level of a operably linked reporter gene is at least 60%, preferably at least 75%, more preferably at least 90% and most preferably at least 100% of the expression level obtained with the SEQ ID NO:8 in a comparative reporter gene assay. Particularly preferred are modified terminators which have a minimum sequence homology to the wild-type sequence SEQ ID NO:8 of the hamster growth hormone polyadenylation signal or its complementary sequence of at least 75%, preferably at least 80%, preferably at least 85%, more preferably at least 95% and most preferably at least 97% and lead to corresponding expression levels in a comparative reporter gene assay.

In a corresponding comparative "reporter gene assay" the terminator fragments to be tested including the reference sequence SEQ ID NO:8 are cloned downstream of a reporter gene. This reporter gene codes, for example for luciferase, secreted alkaline phosphotase or green fluorescent protein (GFP). Alternatively, other polypeptides or proteins, for example an antibody or sICAM, can be used as reporter genes. These constructs are subsequently introduced into the test cells, e.g. CHO-DG44, by transfection and the influence of the modified terminator in question on the expression level of the reporter gene is determined for example by measuring the protein content of the reporter gene. A corresponding test is described in examples 2, 3 and 4 of the present invention.

A preferred HGH polyadenylation signal is the nucleotide sequence comprising the sequence of SEQ ID NO:8 or subsequence thereof comprising the sequence of SEQ ID NO: 9. In other embodiments, the polyadenylation signal is a nucleotide sequence which comprises or consists of a nucleotide sequence with homology or sequence identity to SEQ ID NO:7, SEQ ID NO:8, SEQ ID NO:9 or SEQ ID NO:10. As used herein, two sequences have sequence identity or homology when the nucleotide sequences are homologous or identical by at least 75%, preferably 80%, preferably 85%, more preferably 90%, and even more preferably 95% or more. Substantial identity also exists when the nucleic acid sequence will hybridize under stringent conditions to the complement of the strand.

As used herein, the term "hybridizes under stringent conditions" describes conditions for hybridization and washing which are known to those skilled in the art. Generally, stringent conditions are selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to about 50 nucleotides) and at least about 60° C. for long probes (e.g. greater than about 50 nucleotides). Exemplary stringent conditions include hybridization at 60 to 65° C. in a hybridization buffer with 5×SSC and washing at 42° C. with 0.2×SSC/0.1% SDS. A positive hybridization signal is at least 2 times above background hybridization.

The polyadenylation sequence of the hamster growth hormone and modified terminators, which may also include, for example natural occurring nucleotide sequences further upstream or downstream of the isolated HGH sequence of SEQ ID NO:7 or selected fragments thereof, may be obtained by a skilled artisan with a knowledge of the sequence or homologous sequences using various standard methods known in the art and a suitable method is also described in the present invention in example 1. Starting from the sequence described in SEQ ID NO:7 a suitable fragment may be selected, for example, and an oligonucleotide probe containing the sequence of this fraction may be chemically synthesized. A probe of this kind may be used for example to clone the hamster growth hormone gene or the 3' untranslated region or other fragments thereof, for example by hybridization from a library of the hamster genome. Using the reporter gene assay described above the skilled artisan is in a position to identify functional terminator fragments without any great effort and use them for the purposes of the present invention. The 3' untranslated region or special fragments thereof can easily be obtained by PCR amplification with corresponding primers from genomic DNA or a genomic library. Fragments of the 3' untranslated region may also be obtained by limited exonuclease III digestion from larger DNA fragments. Such DNA molecules may also be chemically synthesized or produced from chemically synthesized fragments by ligation. Deletion, insertion, addition and substitution mutants may be produced by site-specific mutagenesis, PCR-based mutagenesis techniques and/or chemical synthesis known to those skilled in the art. Preferably, a mutant is altered at up to 3, 6, 10, 20 or 50 bp positions. Preferably a mutant is altered at 6 bp positions.

A similar approach as described in the present invention in example 1 can be used to isolate for example the polyadenylation signals of the mouse, rat or syrian hamster growth hormone or growth hormones of other species. Their performance can be tested in reporter gene assays as described in examples 2, 3 or 4 of the present invention. By cross-hybridisation with probes derived from the hamster growth hormone sequence, preferably from the 3' untranslated region, it is also possible to identify and isolate suitable terminator sequences from corresponding homologous genes of other, preferably mammalian, species. Suitable techniques are known to those skilled in the art.

The terms "homology", "homologous", "identity", "identical", "sequence identity" or "homologous sequence" are used interchangeably. Methods for calculating "homology" or "identity" are well known in the art. For sequence comparison typically one sequence acts as a reference sequence to which test sequences are compared. The sequences are aligned for maximal correspondence. Gaps can be introduced in either of the nucleic acid sequences in the comparison for optimal alignment. Percent identity between two sequences is a function of the number of identical positions shared by the sequences, taking into account the number of gaps and the length of each gap which need to be introduced for optimal alignment of the two sequences. The comparison of sequences and determination of percent identity between two sequences can be accomplished using mathematical algorithms. Default program parameters can be used or alternative parameters can be designated. The sequence comparison algorithm then calculates the percent identity for the test sequence(s) relative to the reference sequence, based on the designated or default program parameters. One example of an algorithm that is suitable for determining identity is the BLAST algorithm (Altschul et al., J. Mol. Biol. 215, 403-410, 1990; Gish et al., Nature Genetics 3, 266-272, 1993; Madden et al., Meth. Enzymol. 266, 131-141, 1996; Zhang et al., Genome Res. 7, 649-656, 1997; Altschul et al., Nucleic Acids Res. 25, 3389-3402, 1997). Other computerized implementations of alignment algorithms are GAP, PILEUP, BESTFIT, FASTA and TFASTA in the Wisconsin Genetics Software Package. However, percent identity can be also determined by manual alignment and visual inspection and calculation.

The term "vector" as used herein relates to naturally occurring or synthetically generated constructs for uptake, proliferation, expression or transmission of nucleic acids in a cell, e.g. plasmids, minicircles, phagemids, cosmids, artificial chromosomes/mini-chromosomes, bacteriophages, viruses such as baculovirus, retrovirus, adenovirus, adeno-associated virus, herpes simplex virus, bacteriophages. Methods used to construct vectors are well known to a person skilled in the art and described in various publications. In particular techniques for constructing suitable vectors, including a description of the functional and regulatory components such as promoters, enhancers, termination and polyadenylation signals, selection markers, origins of replication, and splicing signals, are known to the person skilled in the art. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operably linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

A preferred embodiment of the invention are vectors or polynucleotide sequences containing one or more transcription units encoding genes of interest which comprise at least one HGH polyadenylation signal for transcript termination and stabilization and/or as insulating sequence. Also preferred according to the invention are vectors or polynucleotide sequences comprising HGH polyadenylation signals for transcript termination and stabilization and/or as insulating sequence which instead of genes of interest have only a multiple cloning site which allows the cloning of the gene of interest via recognition sequences for restriction endonucleases.

The term "promoter" denotes a polynucleotide sequence which allows and controls the transcription of the genes or sequences operably connected therewith. A promoter contains recognition sequences for binding RNA polymerase and the initiation site for transcription (transcription initiation site). In order to express a desired sequence in a certain cell type or a host cell a suitable functional promoter must be chosen. A large number of promoters, including constitutive, inducible and repressible promoters from a variety of different sources, are well known in the art (and identified in databases such as GenBank) and are available as separate elements or elements cloned within polynucleotide sequences from commercial (e.g. depositories such as ATCC as well as other commercial sources) or individual sources. In inducible promoters the activity of the promoter may be increased or reduced in response to a signal. For example, the tetracycline (tet) promoter containing the tetracycline operator sequence (tetO) can be induced by a tetracycline-regulated transactivator protein (tTA). Binding of the tTA to the tetO is inhibited in the presence of tet. Examples for other inducible promoters are jun, fos, metallothionein and heat shock promoters. Of the promoters which are particularly suitable for high expression in eukaryotes, there are for example the ubiquitin/S27a promoter of the hamster (WO 97/15664), SV 40 early promoter, adenovirus major late promoter, mouse metallothionein-I promoter, the long terminal repeat region of Rous Sarcoma Virus, the early promoter of human Cytomegalovirus (CMV). Examples of other heterologous mammalian promoters are the actin, immunoglobulin or heat shock promoter(s).

The aforementioned promoters are well known in the art. A corresponding heterologous promoter can be functionally connected to other regulatory sequences in order to increase/regulate the transcription activity in an expression cassette. For example, the promoter may be functionally linked to enhancer sequences in order to increase the transcriptional activity. For this, one or more enhancers and/or several copies of an enhancer sequence may be used, e.g. a CMV or SV40 enhancer. Accordingly, an expression vector according to the invention, in another embodiment, contains one or more enhancers/enhancer sequences, preferably a CMV or SV40 enhancer.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The term "transcription termination site" refers to a nucleotide sequence normally represented at the 3' end of the gene of interest or of the stretch of sequences to be transcribed, that causes RNA polymerase to terminate transcription.

A "transcription unit", "expression unit" or "expression cassette" defines a region within a vector, construct or polynucleotide sequence that contains one or more genes to be transcribed, wherein the genes contained within the segment are operably linked to each other. They are transcribed from a single promoter and transcription is terminated by at least one polyadenylation signal. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequence that are contained within the unit. And each transcription unit may contain the same or different regulatory elements. For example, each transcription unit may contain the same terminator. IRES element or introns may be used for the functional linking of the genes within a transcription unit. A vector or polynucleotide sequence may contain more than one transcription unit.

"Translation regulatory elements" comprise a translation initiation site (AUG), a stop codon and a polyA signal for each individual polypeptide to be expressed. An internal ribosome entry site (IRES) may be included in some constructs. IRES is defined below. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence: GCCGCCACCAUGG (SEQ ID NO:13); AUG constitutes the start codon) can be inserted immediately upstream of the start codon to enhance translation and thus expression. Increased A/U contents around this ribosome binding site further a more efficient ribosome binding. To produce a secreted polypeptide the gene of interest usually includes a signal sequence encoding a leader or signal peptide that directs the newly synthesized polypeptide to and through the ER membrane where the polypeptide can be routed for secretion. The leader or signal peptide is often but not universally at the amino terminus of a secreted protein and is cleaved off by signal peptidases after the protein crosses the ER membrane. The gene sequence will generally, but not necessarily, contain its own signal peptide sequence. Where the native signal peptide sequence is absent, a heterologous signal peptide sequence can be fused to the selected sequence. Or the native signal peptide sequence can be replaced be a heterologous one. Numerous signal peptide sequences are known to the skilled artisan and deposited in sequence databanks such as GenBank and EMBL.

An "internal ribosome entry site" or "IRES" describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. encephalomyocarditis virus (EMCV), picornavirus (e.g. FMDV), polio virus (PV), or hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance.

The term "intron" as used herein, refers to a non-coding nucleic acid sequence of varying length, normally present within many eukaryotic genes, which is removed from a newly transcribed mRNA precursor by the process of splicing for which highly conserved sequences at or near either end of the intron are necessary. In general, the process of splicing requires that the 5' and 3' ends of the intron be correctly cleaved and the resulting ends of the mRNA be accurately joined, such that a mature mRNA having the proper reading frame for protein synthesis is produced. Many splice donor and splice acceptors sites, meaning the sequences immediately surrounding the exon-intron- and intron-exon-boundaries, have been characterized and described and are known to the skilled artisan.

The terms "gene of interest", "desired sequence", "polynucleotide of interest" or "desired gene" as used herein have the same meaning and refer to a polynucleotide sequence of any length that encodes a product of interest. The selected sequence can be full length or a truncated gene, a fusion or tagged gene, and can be a cDNA, a genomic DNA, or a DNA fragment. It can be the native sequence, i.e. naturally occurring form(s), or can be mutated or otherwise modified as desired. These modifications include codon optimizations to optimize codon usage in the selected host cell, humanization or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

Within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. using PCR methodology, by ligation at suitable restrictions sites or by annealing. Synthetic oligonucleotide linkers or adaptors can be used in accord with conventional practice if suitable restriction sites are not present.

The term "nucleic acid", "nucleic acid sequence", "nucleotide sequence", "polynucleotide", "polynucleotide sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The term "encoding" or "coding" refers to the inherent property of specific sequences of nucleotides in a nucleic acid, such as a gene in chromosome or an mRNA, to serve as templates for synthesis of other polymers and macromolecules in biological processes having a defined sequence of nucleotides (i.e. rRNA, tRNA, other RNA molecules) or amino acids and the biological properties resulting therefrom. Accordingly, a gene codes for a protein if the desired protein is produced in a cell or another biological system by transcription and subsequent translation of the mRNA. Both the coding strand, the nucleotide sequence of which is identical to the mRNA sequence and is usually provided in sequence listings of databanks, e.g. EMBL or GenBank, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns. In the Sequence Listing the sequences are presented as DNA rather than RNA sequence. For example, when presented as DNA the start codon is presented as ATG rather than AUG.

The term "cDNA" in the context of this invention refers to deoxyribonucleic acids produced by reverse transcription and typically second-strand synthesis of mRNA or other RNA produced by a gene. If double-stranded, a cDNA molecule has both a coding or sense and a non-coding or antisense strand.

The term "expression" as used herein refers to transcription and/or translation of a heterologous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods, e.g. by ELISA, by Western blotting, by radioimmunoassays, by immunoprecipitation, by assaying for the biological activity of the protein, or by immunostaining of the protein followed by FACS analysis PCR.

The term "polypeptide" is used interchangeably with "amino acid residue sequence" or the term "protein" and refers to polymers of amino acids of any length. These terms also include proteins that are post-translationally modified through reactions that include, but are not limited to glycosylation, glycation, acetylation, phosphorylation, oxidation, amidation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties. Amino acid modifications can be prepared for example by performing site-specific mutagenesis or polymerase chain reaction mediated mutagenesis on its underlying nucleic acid sequence. The term "polypeptide" thus also includes, for example, fusion proteins consisting of an immunoglobulin component, e.g. the Fc component, and a growth factor, e.g. an interleukin.

As used herein, the term "antibody" includes a polyclonal, monoclonal, bi-specific, multi-specific, human, humanized, or chimeric antibody, a single chain antibody, an antigen-binding fragment of an antibody (e.g., an Fab or F(ab')$_2$ fragment), a disulfide-linked Fv, etc. Such antibodies may be produced through chemical synthesis, via recombinant or transgenic means, via cell (e.g., hybridoma) culture, or by other means.

Fab fragments (Fragment antigen-binding=Fab) consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind are known from the prior art.

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins are known from the prior art.

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins are known from the prior art.

By triabody the skilled person means a: trivalent homotrimeric scFv derivative. ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures. In a preferred embodiment of the present invention, the gene of interest is encoded for any of those desired polypeptides mentioned above, preferably for a monoclonal antibody, a derivative or fragment thereof.

The "polypeptide of interest", "protein of interest" or "product of interest" includes proteins, polypeptides, fragments thereof, peptides, fusion proteins all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use.

Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1, VEGF and nanobodies. Also included is the production of erythropoietin or any other hormone growth factors and any other polypeptides that can serve as agonists or antagonists and/or have therapeutic or diagnostic use. The method according to the invention can also be advantageously used for production of antibodies, such as monoclonal, polyclonal, multispecific and single chain antibodies, or fragments thereof, e.g. Fab, Fab', F(ab')2, Fc and Fc'-fragments, heavy and light immunoglobulin chains and their constant, variable or hypervariable region as well as Fv- and Fd-fragments.

The "product of interest" may also be an antisense RNA, tRNA, rRNAs, other RNAs being part of riboproteins or other regulatory RNAs.

The method of the present invention may be performed in all eukaryotic cells. Cells and cell lines may be present e.g. in a cell culture and include but are not limited to eukaryotic cells, such as yeast, plant, insect or mammalian cells. For example, the cells may be oocytes, embryonic stem cells, hematopoietic stem cells or any type of differentiated cells. A method is preferred wherein the eukaryotic cell is a mammalian cell. More preferred is a method wherein the mammalian cell is a human, simian, murine, rat, rabbit, hamster, goat, bovine, sheep or pig cell. Preferred cell lines or "host cells" for the production of biopharmaceuticals are human, mice, rat, monkey, or rodent cell lines. More preferred are hamster cells, preferably BHK21, BHK TK⁻, CHO, CHO-K1, CHO-DUKX, CHO-DUKX B1, CHO-S and CHO-DG44 cells or the derivatives/progenies of any of such cell lines. Particularly preferred are CHO-DG44, CHO-DUKX, CHO-K1, CHO-S and BHK21, and even more preferred CHO-DG44 and CHO-DUKX cells. Furthermore, murine myeloma cells, preferably NSO and Sp2/0 cells or the derivatives/progenies of any of such cell lines are also known as production cell lines for biopharmaceutical proteins. Examples of murine and hamster cells which can be used in the meaning of this invention are summarized in Table 1.

TABLE 1

Eukaryotic production cell lines

| CELL LINE | ORDER NUMBER |
| --- | --- |
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (=CHO duk⁻, CHO/dhfr⁻) | ATCC CRL-9096 |
| CHO-DUKX B11 | ATCC CRL-9010 |
| CHO-DG44 | Urlaub et al., Cell 33 (2), 405-412, 1983 |
| CHO Pro-5 | ATCC CRL-1781 |
| CHO-S | Invitrogen Cat No. 10743-029 |
| Lec13 | Stanley P. et al, Ann. Rev. Genetics 18, 525-552, 1984 |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| Per.C6 | Fallaux, F.J. et al, *Human Gene Therapy* 9 (13), 1909-1917, 1998 |
| CHL | ECACC No. 87111906 |

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-SFMII (Invtirogen), serum-free CHO Medium (Sigma), protein-free CHO Medium (Sigma), EX-CELL Media (SAFC), CDM4CHO and SFM4CHO (HyClone) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing a selectable gene a suitable selection agent is added to the culture medium.

The "transfection" of eukaryotic host cells with polynucleotide sequences or expression vectors, resulting in genetically modified cells, recombinant or transgenic cells, can be performed by any method well known to the skilled artisan. Transfection methods include but are not limited to liposome-mediated transfection, calcium phosphate co-precipitation, electroporation, polycation (e.g. DEAE dextran)-mediated transfection, protoplast fusion, microinjection and viral infections. Preferably, the transfection is a stable transfection. The transfection method that provides optimal transfection frequency and expression of the heterologous genes or polynucleotides in the particular host cell line and type is favored. Suitable methods can be determined by routine procedures. For stable transfectants the constructs are either integrated into the host cell's genome or an artificial chromosome/mini-chromosome or located episomally so as to be stably maintained within the host cell. For generation of genetically modified cells expressing the product(s) of interest all required heterologous genes can be located on a single vector or polynucleotide sequence in mono- or multicistronic transcription units. In this case the host cell is transfected with single vectors or polynucleotide sequences. The heterologous genes can also be positioned on different vectors or polynucleotide sequences. In this case host cells are either co-transfected with all vectors or polynucleotide sequences and/or are transfected in successive rounds with the vectors or polynucleotide sequences encoding the genes of interest.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, a hamster actin gene introduced into a hamster host cell is by definition a heterologous gene.

The term "endogenous" means naturally being contained in the cell or organism. An endogenous gene is accordingly a gene which is found in the genome of the un-manipulated wild type cell.

The term "selection marker gene" refers to a gene that only allows cells carrying the gene to be specifically selected for or against in the presence of a corresponding selection agent. By way of illustration, an antibiotic resistance gene can be used as a positive selectable marker gene that allows the host cell transformed with the gene to be positively selected for in the presence of the corresponding antibiotic; a non-transformed host cell would not be capable of growth or survival under the selection culture conditions. Selectable markers can be positive, negative or bifunctional. Positive selectable markers allow selection for cells carrying the marker by conferring resistance to a drug or compensate for a metabolic or catabolic defect in the host cell. In contrast, negative selection markers allow cells carrying the marker to be selectively eliminated. For example, using the HSV-tk gene as a marker will make the cells sensitive to agents such as acyclovir and gancyclovir. The selectable marker genes used herein, including the amplifiable selectable genes, will include recombinantly engineered mutants and variants, fragments, functional equivalents, derivatives, homologs and fusions of the native selectable marker gene so long as the encoded product retains the selectable property. Useful derivatives generally have substantial sequence similarity (at the amino acid level) in regions or domains of the selectable marker associated with the selectable property. A variety of marker genes, well known to the skilled artisan, have been described, including bifunctional (i.e. positive/negative) markers (see e.g. WO 92/08796 and WO 94/28143), incorporated by reference herein. For example, selectable genes commonly used with eukaryotic cells include the genes for aminoglycoside phosphotransferase (APH), hygromycin phosphotransferase (HYG), dihydrofolate reductase (DHFR), thymidine kinase (TK), glutamine synthetase, asparagine synthetase, and genes encoding resistance to neomycin (G418), puromycin, histidinol D, bleomycin and phleomycin.

The "selectable amplifiable marker gene" usually encodes an enzyme which is required for growth of eukaryotic cells under those conditions. For example, the selectable amplifiable marker gene may encode DHFR which gene is amplified when a host cell transfected therewith is grown in the presence of the selective agent, methotrexate (MTX). Accordingly, host cells genetically modified according to any method described herein are encompassed by this invention, wherein the selectable amplifiable marker gene encodes for example for a polypeptide having the function of dihydrofolate reductase (DHFR), glutamine synthetase, CAD, adenosine deaminase, adenylate deaminase, UMP synthetase, IMP 5'-dehydrogenase, xanthine guanine phosphoribosyl transferase, HGPRTase, thymidine kinase, thymidylate synthetase, P glycoprotein 170, ribonucleotide reductase, asparagine synthetase, arginosuccinate synthetase, ornithine decarboxylase, HMG CoA reductase, acetylglucosaminyl transferase, threonyl-tRNA synthetase or $Na^+K^+$-ATPase. For a review of the exemplary selectable amplifiable marker genes listed in Table 2 see Kaufman, Methods in Enzymology, 185, 537-566, 1990.

One particular selectable amplifiable marker gene is the gene encoding dihydrofolate reductase (DHFR) which is necessary for the biosynthesis of purines. Cells lacking the DHFR gene will not grow on medium lacking purines. The DHFR gene is therefore useful as a dominant selectable marker to select and amplify genes in such cells growing in medium lacking purines. The selection agent used in conjunction with a DHFR gene is methotrexate (MTX).

Another selection and/or amplification marker is the glutamine synthetase (GS) gene. The GS gene encodes the glutamine synthetase enzyme which is required for synthesis of the amino acid glutamine. Cells lacking the GS gene or expressing low endogenous GS levels will not grow in glutamine-free media. The GS gene is therefore useful as a dominant selectable marker to select and amplify genes in such cells growing in glutamine-free medium. The selection agent used in conjunction with the GS gene is methionine sulfoximine (MSX).

TABLE 2

Selectable amplifiable marker genes

| Selectable Amplifiable Marker Gene | Accession Number | Selection Agent |
|---|---|---|
| Dihydrofolate reductase | M19869 (hamster) E00236 (mouse) | Methotrexate (MTX) |
| Metallothionein | D10551 (hamster) M13003 (human) M11794 (rat) | Cadmium |
| CAD (Carbamoyl-phosphate synthetase: Aspartate transcarbamylase: Dihydroorotase) | M23652 (hamster) D78586 (human) | N-Phosphoacetyl-L-aspartate |
| Adenosine deaminase | K02567 (human) M10319 (mouse) | Xyl-A- or adenosine, 2'deoxycoformycin |
| AMP (adenylate) deaminase | D12775 (human) J02811 (rat) | Adenine, azaserine, coformycin |
| UMP synthase | J03626 (human) | 6-Azauridine, pyrazofuran |
| IMP 5'dehydrogenase | J04209 (hamster) J04208 (human) M33934 (mouse) | Mycophenolic acid |
| Xanthine-guanine phosphoribosyltransferase | X00221 (E. coli) | Mycophenolic acid with limiting xanthine |
| Mutant HGPRTase or mutant thymidine kinase | J00060 (hamster) M13542, K02581 (human) J00423, M68489 (mouse) M63983 (rat) | Hypoxanthine, aminopterin, and thymidine (HAT) |

TABLE 2-continued

Selectable amplifiable marker genes

| Selectable Amplifiable Marker Gene | Accession Number | Selection Agent |
|---|---|---|
| Thymidylate synthetase | M36160 (herpesvirus) D00596 (human) M13019 (mouse) L12138 (rat) | 5-Fluorodeoxyuridine |
| P-glycoprotein 170 (MDR1) | AF016535 (human) J03398 (mouse) | Multiple drugs, e.g. adriamycin, vincristine, colchicine |
| Ribonucleotide reductase | M124223, K02927 (mouse) | Aphidicolin |
| Glutamine synthetase | AF150961 (hamster) U09114, M60803 (mouse) M29579 (rat) | Methionine sulfoximine (MSX) |
| Asparagine synthetase | M27838 (hamster) M27396 (human) U38940 (mouse) U07202 (rat) | β-Aspartyl hydroxamate, Albizziin, 5'Azacytidine |
| Argininosuccinate synthetase | X01630 (human) M31690 (mouse) M26198 (bovine) | Canavanine |
| Ornithine decarboxylase | M34158 (human) J03733 (mouse) M16982 (rat) | α-Difluoromethylornithine |
| HMG-CoA reductase | L00183, M12705 (hamster) M11058 (human) | Compactin |
| N-Acetylglucosaminyl transferase | M55621 (human) | Tunicamycin |
| Threonyl-tRNA synthetase | M63180 (human) | Borrelidin |
| $Na^+ K^+$-ATPase | J05096 (human) M14511 (rat) | Ouabain |

Selection may also be made by fluorescence activated cell sorting (FACS) using for example a cell surface marker, bacterial β-galactosidase or fluorescent proteins (e.g. green fluorescent proteins (GFP) and their variants from *Aequorea victoria* and *Renilla reniformis* or other species; red fluorescent proteins, fluorescent proteins and their variants from non-bioluminescent species (e.g. *Discosoma* sp., *Anemonia* sp., *Clavularia* sp., *Zoanthus* sp.) to select for recombinant cells.

The term "selection agent" refers to a substance that interferes with the growth or survival of a host cell that is deficient in a particular selectable gene. For example, to select for the presence of an antibiotic resistance gene like APH (aminoglycoside phosphotransferase) in a transfected cell the antibiotic Geneticin (G418) is used. The selection agent can also comprise an "amplifying agent" which is defined for purposes herein as an agent for amplifying copies of the amplifiable gene if the selectable marker gene relied on is an amplifiable selectable marker. For example, MTX is a selection agent useful for the amplification of the DHFR gene.

A further embodiment of the above mentioned methods relates to a method, wherein the polypeptide(s)/product(s) which is/are encoded by the gene(s) of interest and being expressed in said host cell, is/are isolated from the cells or the cell culture supernatant, if secreted into the culture medium.

Said production cells are cultivated preferentially in serum-free medium and in suspension culture under conditions which are favorable for the expression of the desired gene(s) and isolating the protein of interest from the cells and/or the cell culture supernatant. Preferably the protein of interest is recovered from the culture medium as a secreted polypeptide, or it can be recovered from host cell lysates if expressed without a secretory signal. It is necessary to purify the protein of interest from other recombinant proteins, host cell proteins and contaminants in a way that substantially homogenous preparations of the protein of interest are obtained. As a first step often cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a heterologous protein expressed by host cells, are well known in the art.

The practice of the present invention will employ, unless otherwise indicated, conventional techniques of cell biology, molecular biology, cell culture, immunology and the like which are in the skill of one in the art. These techniques are fully disclosed in the current literature.

The following examples are not limiting. They merely show possible embodiments of the invention. A person skilled in the art could easily adjust the conditions to apply it to other embodiments.

EXAMPLES

Abbreviations

AP: Alkaline phosphatase
BGH: Bovine growth hormone
bp: Base pair
CHO: Chinese hamster ovary
DHFR: Dihydrofolate reductase
ELISA: Enzyme-linked immunosorbant assay
FACS: Fluorescence-activated cell sorter
HGH: Hamster growth hormone
HT: Hypoxanthine/thymidine
HRPO: Horseradish peroxidase
IgG: Immunoglobuline
IRES: Internal ribosomal entry site
kb: Kilobase
mAb: Monoclonal antibody
MTX: Methotrexate
NPT: Neomycin phosphotransferase
nt: Nucleotides
PBS: Phosphate buffered saline
PCR: Polymerase chain reaction
SEAP: Secreted alkaline phosphatase
sICAM: Soluble intracellular adhesion molecule
UTR: Untranslated region
Materials and Methods
Cell Culture CHO-DG44/dhfr$^{-/-}$ cells are grown permanently in suspension in the serum-free medium CHO-S-SFMII (Invitrogen) supplemented with hypoxanthine and thymidine (HT). Cells are incubated in cell culture flasks at 37° C. in a humidified atmosphere containing 5% $CO_2$. The cell number as well as the cell viability are determined with a CASY1 Cell Counter (Schaerfe System, Germany), a Cedex (Innovatis AG, Germany) or via trypan blue dye exclusion. Cells are seeded at a concentration of 1-3×10$^5$ cells/mL in fresh medium every two to three days.
Transfections Transfections of CHO-DG44 cells are conducted using Lipofectamine Plus reagent (Invitrogen). Per transfection 6×10$^5$ exponentially growing cells in 0.8 mL hypoxanthine/thymidine (HT)-supplemented CHO-S-SFMII medium are seeded in a well of a 6-well chamber. A mixture of plasmid DNA, 4 μL Lipofectamine and 6 μL Plus reagent in a volume of 200 μL is generated for each transfection and added to the cells, following the protocol of the manufacturer. After incubation for 3 hours 2 mL of HT-supplemented CHO-S-SFMII medium is added.

Figure 1:
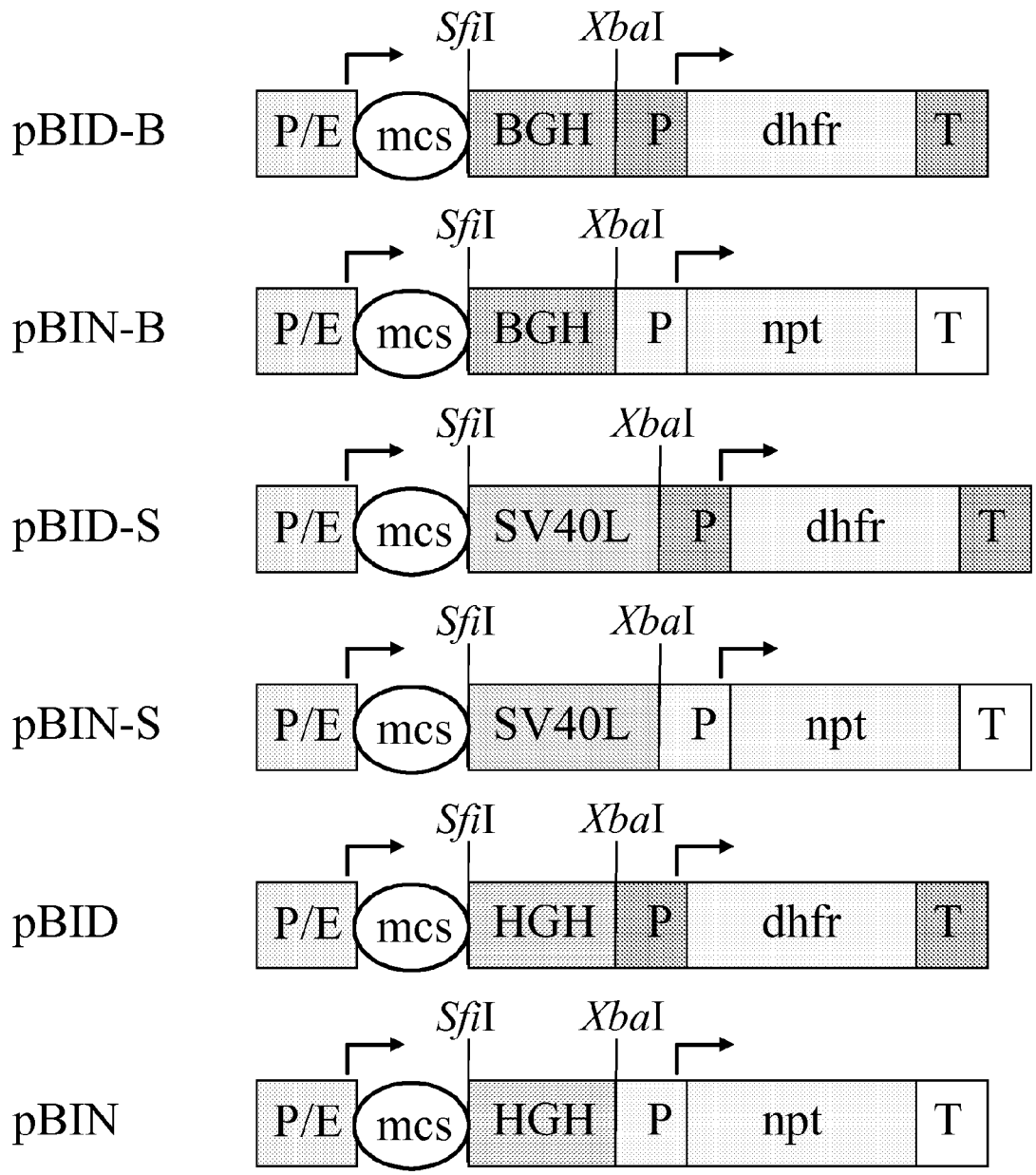
FIG. 1: Basic Expression Vectors

Transient transfections are performed in triplicate and supernatant and cells are harvested 2 days post transfection. For a DHFR-based selection of stable transfected CHO-DG44 cells the medium is replaced with HT-free CHO-S-SFMII medium 48 hours post transfection. DHFR-based gene amplification is achieved by adding MTX in the range of 5-2000 nM (Sigma) as amplifying selection agent to the medium. In case of co-transfections a DHFR- and NPT-based selection of stable transfected CHO-DG44 cells is performed by transferring the cells 48 hours post transfection into HT-free CHO-S-SFMII medium supplemented with G418 (Invitrogen) in a concentration of 200-400 μg/mL.
Expression Vectors Eukaryotic expression vectors are derivatives of the pAD-CMV1 vector (WO 9201055) and mediate constitutive expression of the heterologous genes driven by the CMV promoter/enhancer. For termination and polyadenylation of the transcript of the gene of interest vectors contain either the SV40 late polyadenylation signal (SEQ ID NO: 11) or the BGH polyadenylation signal (SEQ ID NO: 12). pBID vectors encode a DHFR mini gene as amplifiable selection marker (see for example EP 0 393 438) whereas pBIN vectors encode a NPT gene as selection marker under the control of the SV40 early promoter and a thymidine kinase polyadenylation signal (FIG. 1).

Genes of interest encoding for human sICAM, heavy and light chain of monoclonal antibodies (IgG1, IgG2 or IgG4 isotype) or Fc fusion proteins are cloned into the vectors using the multiple cloning sites located between promoter and polyadenylation signal.
ELISA sICAM titers are quantified by ELISA with standard protocols using two in house developed sICAM specific monoclonal antibodies (as described for example in U.S. Pat. Nos. 5,284,931 and 5,475,091), whereby one of the antibodies is a HRPO-conjugated antibody. Purified sICAM protein is used as a standard.

mAb titers are quantified by ELISA with standard protocols using an goat anti-human IgG Fc fragment (Dianova) and an AP-conjugated goat anti-human kappa light chain antibody (Sigma). Purified mAb antibody of the same isotype as the expressed mAb is used as standard.

Samples are analyzed using a Spectra Fluor Plus reader (TECAN, Crailsheim, Germany).

Cell productivity (pg/cell/day) is calculated with the formula pg/((Ct−Co)t/ln (Ct−Co)) whereby "Co" is the cell number at the time of seeding, "Ct" the cell number at the time of harvest and "t" the cultivation period.
SEAP Assay SEAP activity is determined with the SEAP Reporter Gene Assay according to the protocol of the manufacturer (Roche Diagnostics).

Example 1

Isolation and Cloning of the Transcriptional Termination Region of the Hamster Growth Hormone (HGH)

For the isolation of the complete polyadenylation signal region of the growth hormone gene from CHO-DG44 genome (chinese hamster, *Cricetus griseus*) an adapter-ligated genomic CHO-DG44 DNA serves as template in a nested PCR. The primary PCR is conducted with a primer combination with complementarity to the adapter sequence and a growth hormone gene sequence, respectively. The gene specific primer GH for1 (5'-GAGACCTACCTGCGGGTCA TGA-3'; SEQ ID NO: 1) is designed on basis of a cDNA sequence of the growth hormone of the syrian hamster (*Mesocricetus auratus*; Genbank S66299) and is located 35 bp upstream of the stop codon. A secondary PCR is performed on the primary PCR products with a combination of an inner adaptor primer and a second, nested gene specific primer GH for2; 5'-AGTGCCGTCGCTTTGTGGAAA G-3'; SEQ ID NO: 2), positioned directly downstream of the GH for1 primer position. The resulting DNA fragments are subcloned in a TA cloning vector (Invitrogen) and further analyzed by sequence analysis. The longest DNA fragment contains aside of the GH for2 primer sequence further 13 bp of the 3' end of the coding region followed by a stop codon and 324 bp of the 3' untranslated region of the growth hormone of *Cricetus griseus* (FIG. 2; SEQ ID NO: 7).

To obtain just the 3' untranslated region with in total 324 bp (SEQ ID NO: 8) another PCR is performed using the primers GH Sfi for1 (SEQ ID NO: 3) and GH Xba rev1 (SEQ ID NO: 4). Thereby the above mentioned 362 bp DNA fragment (SEQ ID NO: 7), subcloned in the TA vector, serves as template in the PCR. The amplified sequence (SEQ ID NO:8) has the following homologies to the growth hormone 3' untranslated regions of various species: 72.1% to the sequence of the syrian hamster *Mesocricetus auratus* (Genbank S66299), 71.6% to the sequence of *Mus musculus* (Genbank Z46663), 61% to the sequence of *Rattus norvegicus* (Genbank V01239) and 50.4% to the BGH sequence of *Bos taurus* (Genbank J00008) (FIG. 3).

The PCR-based approach is also used for the generation of subclones with various deletions of the 3' end of the isolated 3' untranslated region. Using the primer combination GH Sfi for 1 (SEQ ID NO: 3) and GH Xba rev2 (SEQ ID NO: 5) a 189 bp fragment of the 3' untranslated region is generated (SEQ ID NO: 9) and with the primer combination GH Sfi for 1 (SEQ ID NO: 3) and GH Xba rev3 (SEQ ID NO: 6) a 113 bp subfragment is generated (SEQ ID NO: 10). Thus, all amplified fragments of the 3' untranslated region have an identical 5' end which corresponds to the first nucleotide after the stop codon and a variable 3' end (FIG. 4).

PCR products are digested with SfiI and XbaI and the resulting restriction fragments are used to replace the SV40 late polyadenylation signal sequence in the vector pJR106, which encodes human sICAM (FIG. 5). The resulting vectors pJR131, pJR134 and pJR135 contain now a polyadenylation signal sequence derived from the growth hormone of *Cricetus griseus*, called for short HGH, with a size of 324 bp (SEQ ID NO: 8), 189 bp (SEQ ID NO: 9) and 113 bp (SEQ ID NO: 10), respectively (FIG. 5).

Example 2

Impact of HGH Polyadenylation Signal Se-Quence on the Transient Expression of sICAM To evaluate the impact of the polyadenylation signal sequence derived from the *Cricetus griseus* growth hormone (HGH) on the expression of a gene of interest, sICAM, independent of chromosomal integration sites transient transfections are performed. CHO-DG44 cells are transfected with the plasmid pJR131 which contains 324 bp of the 3' UTR of the hamster growth hormone (=HGH, SEQ ID NO: 8) (FIG. 5). Vectors containing either the SV40 late (pJR106) or the BGH (pJR110) polyadenylation signal sequences are used as control (FIG. 5). Apart from the different termination sequences the genetic setup of the various vectors for the expression of sICAM is identical.

Supernatants are harvested 2 days post transfection and the sICAM titers determined using ELISA. To correct for transfection efficiency cells are co-transfected with the plasmid pCMV-SEAP (100 ng DNA/transfection reaction), which encodes the secreted alkaline phosphatase, and the SEAP activity is measured.

FIG. 6 shows the data of 2 independent transient transfection series performed in duplicate. Surprisingly, the highest sICAM expression is obtained with the polyadenylation signal sequence derived from the growth hormone gene of hamster. The titer is increased up to 21% (transfection series #1) compared to cells transfected with the vector pJR110 containing the BGH polyadenylation signal and increased up to 40% (transfection series #1) compared to cells transfected with the vector pJR106 containing the SV40 late polyadenylation signal.

Example 3

Impact of HGH Polyadenylation Signal on the Transient Expression of an IgG4 Antibody To evaluate the impact of the polyadenylation signal sequence derived from the *Cricetus griseus* growth hormone (HGH) on the expression of a gene of interest, humanized IgG4/kappa mAb, independent of chromosomal integration sites transient transfections are performed. CHO-DG44 cells are co-transfected with the vector combination pBID/IgG4 and pBIN/kappa. Both vectors contain 324 bp of the 3' UTR of the hamster growth hormone (=HGH; SEQ ID NO: 8) as a polyadenylation signal sequence. As a control CHO-DG44 cells are co-transfected with the vector combination pBID-B/ IgG4 and pBIN-B/kappa which contain the BGH polyadenylation signal (see FIG. 1 for basic vectors). Aside of the different termination sequences the genetic setup of the various vectors for the expression of the IgG4/kappa mAb is identical.

Supernatants are harvested 2 days post transfection and the IgG4 titers determined using ELISA. Per vector combination 6 cell pools are transfected. To correct for transfection efficiency cells are co-transfected with the plasmid pCMV-SEAP (100 ng DNA/transfection reaction), which encodes the secreted alkaline phosphatase, and the SEAP activity is measured.

Surprisingly, titers obtained with the HGH polyadenylation signal sequence are on average 35% higher than for the BGH polyadenylation signal (FIG. 7).

Example 4

Test of Different HGH Variants

Two 3' deletion clones of the 324 bp HGH sequence derived from the *Cricetus griseus* growth hormone (SEQ ID NO: 8) are generated by PCR and placed as a polyadenylation signal sequence downstream of the sICAM gene. The resulting vectors pJR134 and pJR135 (FIG. 5) contain a shorter stretch of the HGH sequence of 189 bp (SEQ ID NO: 9) and 113 bp (SEQ ID NO: 10), respectively, which have a common 5' end position (FIG. 4).

To evaluate the impact of the HGH deletion variants on the expression of a gene of interest, sICAM, independent of chromosomal integration sites transient transfections are performed. CHO-DG44 cells are transfected with the vectors pJR134 and pJR135. Vector pJR131 containing the 324 bp HGH sequence is used as control (FIG. 5). Aside of the different termination sequences the genetic setup of the various vectors for the expression of sICAM is identical. Supernatants are harvested 2 days post transfection and the sICAM titers determined using ELISA. To correct for transfection efficiency cells are co-transfected with the plasmid pCMV-SEAP (100 ng DNA/transfection reaction), which encodes the secreted alkaline phosphatase, and the SEAP activity is measured.

FIG. 8 shows the data of 2 independent transient transfection series performed in duplicate. Both HGH deletion variants lead to reduced sICAM expression levels. The HGH sequence of 189 bp contained in the expression vector pJR134 results in a more moderate reduction of up to 23%. Thus the 189 bp fragment shows a performance comparable to the BGH and SV40 late polyadenylation signal (see example 2 and 3). However, the shortest HGH sequence of 113 bp contained in the expression vector pJR135 leads to a up to 78% reduced sICAM expression. This shows that between the HGH region of by 190 to 324 of SEQ ID NO:8 sequences are located which contribute to an efficient expression of a gene interest.

Example 5

Stable Expression of Proteins at High Levels Using the HGH Polyadenylation Signal CHO-DG44 cells are co-transfected with vector combinations encoding either for the heavy and light chain of mAbs of various isotypes (IgG1, IgG2, IgG4) or for Fc fusion proteins whereby the Fc part is derived from IgG1 or IgG2. The basic vectors pBID and pBIN (FIG. 1) used for expression contain the 324 bp HGH sequence (SEQ ID NO:8) as polyadenylation signal sequence positioned downstream of the gene of interest. Stable cell pools are selected using a DHFR- and NPT-based selection 2 days post transfection. The first selection of stable transfectants is followed by two successive DHFR-mediated gene amplification steps by adding to the culture medium 100 nM MTX in the first round and subsequently 800 nM MTX. Single cell clones are obtained either by dilution cloning or a FACS-based deposition of single cells into wells of a 96 well plate.

The experimental data show that high expression of a protein of interest in stable transfectants can be achieved using the HGH polyadenylation signal from *Cricetus griseus*. Cell pools and cell clones with specific productivities in the range of 10-45 pg/cell/day and titers in fed batch processes of up to 6.3 g/L are obtained (FIG. 9).

| SEQUENCE TABLE: | |
|---|---|
| SEQ ID NO: 1 | Primer GH for1 |
| SEQ ID NO: 2 | Primer GH for2 |
| SEQ ID NO: 3 | Primer GH Sfi for1 |
| SEQ ID NO: 4 | Primer GH Xba rev1 |
| SEQ ID NO: 5 | Primer GH Xba rev2 |
| SEQ ID NO: 6 | Primer GH Xba rev3 |
| SEQ ID NO: 7 | Cricetus griseus, growth hormone sequence, part of 3'coding region and 3' untranslated region (362 nucleotides) |
| SEQ ID NO: 8 | Cricetus griseus, 3' untranslated region of growth hormone (324 nucleotides) |
| SEQ ID NO: 9 | Cricetus griseus, 3' untranslated region of growth hormone (189 nucleotides) |
| SEQ ID NO: 10 | Cricetus griseus, 3' untranslated region of growth hormone (113 nucleotides) |
| SEQ ID NO: 11 | SV40, late termination and polyadenylation sequence (222 nucleotides) |
| SEQ ID NO: 12 | Bos taurus, termination and polyadenylation sequence of growth hormone (208 nucleotides) |
| SEQ ID NO: 13 | Kozak sequence, consensus ribosome binding site (13 nucleotides) |

SEQUENCE LISTING

```
<160> NUMBER OF SEQ ID NOS: 13

<210> SEQ ID NO 1
<211> LENGTH: 22
<212> TYPE: DNA
<213> ORGANISM: Artificial
<220> FEATURE:
<223> OTHER INFORMATION: Primer GH for1

<400> SEQUENCE: 1
gagacctacc tgcgggtcat ga                                            22

<210> SEQ ID NO 2
<211> LENGTH: 22
<212> TYPE: DNA
<213> ORGANISM: Artificial
<220> FEATURE:
<223> OTHER INFORMATION: Primer GH for2

<400> SEQUENCE: 2
agtgccgtcg ctttgtggaa ag                                            22

<210> SEQ ID NO 3
<211> LENGTH: 40
<212> TYPE: DNA
```

<213> ORGANISM: Artificial
<220> FEATURE:
<223> OTHER INFORMATION: Primer GH Sfi for1

<400> SEQUENCE: 3
atgcagaggc ctaattggcc cagcggcgtc tctgctggac                              40

<210> SEQ ID NO 4
<211> LENGTH: 36
<212> TYPE: DNA
<213> ORGANISM: Artificial
<220> FEATURE:
<223> OTHER INFORMATION: Primer GH Xba rev1

<400> SEQUENCE: 4
ctagtctaga tatactttat gggggtgaca taggac                                  36

<210> SEQ ID NO 5
<211> LENGTH: 30
<212> TYPE: DNA
<213> ORGANISM: Artificial
<220> FEATURE:
<223> OTHER INFORMATION: Primer GH Xba rev2

<400> SEQUENCE: 5
ctagtctaga gggctgttct tccagcagcc                                         30

<210> SEQ ID NO 6
<211> LENGTH: 35
<212> TYPE: DNA
<213> ORGANISM: Artificial
<220> FEATURE:
<223> OTHER INFORMATION: Primer GH Xba rev3

<400> SEQUENCE: 6
ctagtctaga aatacatcta gccaagcaat acaat                                   35

<210> SEQ ID NO 7
<211> LENGTH: 362
<212> TYPE: DNA
<213> ORGANISM: Cricetulus griseus

<400> SEQUENCE: 7
agtgccgtcg ctttgtggaa agcagctgtg cctttagca gcggcgtctc tgctggactc         60
cccagcgccc cccttaccc tggcaactgc ccaccccta gctttgccct aataaaatga         120
agatgcattg tattgcttgg ctagatgtat ttctgttgtg ggatggaggg tggtgtcaaa       180
gagtcctaga ggccgacatg cctgtgggct gctggaagaa cagccctgac tttgcctgga      240
ccaagtagag tcaacacatc acttcccctg tctcgtgatg agcctgctcc cactccagag      300
tcagaatccc agctctctgg acagtcacaa ggcggcaagg tcctatgtca ccccataaa       360
gt                                                                      362

<210> SEQ ID NO 8
<211> LENGTH: 324
<212> TYPE: DNA
<213> ORGANISM: Cricetulus griseus

<400> SEQUENCE: 8
cagcggcgtc tctgctggac tccccagcgc ccccctttac cctggcaact gcccacccct       60
atgctttgcc ctaataaaat gaagatgcat tgtattgctt ggctagatgt atttctgttg      120
tgggatggag ggtggtgtca agagtccta gaggccgaca tgcctgtggg ctgctggaag      180

```
aacagccctg actttgcctg gaccaagtag agtcaacaca tcacttcccc tgtctcgtga      240
tgagcctgct cccactccag agtcagaatc ccagctctct ggacagtcac aaggcggcaa      300
ggtcctatgt caccccata aagt                                              324
```

<210> SEQ ID NO 9
<211> LENGTH: 189
<212> TYPE: DNA
<213> ORGANISM: Cricetulus griseus

<400> SEQUENCE: 9

```
cagcggcgtc tctgctggac tccccagcgc ccccctttac cctggcaact gcccacccct       60
atgctttgcc ctaataaaat gaagatgcat tgtattgctt ggctagatgt atttctgttg      120
tgggatggag ggtggtgtca aagagtccta gaggccgaca tgcctgtggg ctgctggaag      180
aacagccct                                                              189
```

<210> SEQ ID NO 10
<211> LENGTH: 113
<212> TYPE: DNA
<213> ORGANISM: Cricetulus griseus

<400> SEQUENCE: 10

```
cagcggcgtc tctgctggac tccccagcgc ccccctttac cctggcaact gcccacccct       60
atgctttgcc ctaataaaat gaagatgcat tgtattgctt ggctagatgt att             113
```

<210> SEQ ID NO 11
<211> LENGTH: 222
<212> TYPE: DNA
<213> ORGANISM: Simian virus 40

<400> SEQUENCE: 11

```
cagacatgat aagatacatt gatgagtttg gacaaaccac aactagaatg cagtgaaaaa       60
aatgctttat ttgtgaaatt tgtgatgcta ttgctttatt tgtaaccatt ataagctgca      120
ataaacaagt taacaacaac aattgcattc attttatgtt tcaggttcag ggggaggtgt      180
gggaggtttt ttaaagcaag taaaacctct acaaatgtgg ta                        222
```

<210> SEQ ID NO 12
<211> LENGTH: 208
<212> TYPE: DNA
<213> ORGANISM: Bos taurus

<400> SEQUENCE: 12

```
ctgtgccttc tagttgccag ccatctgttg tttgcccctc cccgtgcctt ccttgaccc       60 tggaaggtgc cactcccact gtcctttcct aataaaatga ggaaattgca tcgcattgtc      120
tgagtaggtg tcattctatt ctggggggtg ggtgggca ggacagcaag ggggaggatt       180
gggaagacaa tagcaggcat gctgggga                                         208
```

<210> SEQ ID NO 13
<211> LENGTH: 13
<212> TYPE: DNA
<213> ORGANISM: Artificial
<220> FEATURE:
<223> OTHER INFORMATION: Kozak sequence consensus ribosome binding site

<400> SEQUENCE: 13

```
gccgccacca tgg                                                          13
```

The invention claimed is:

1. An isolated polyadenylation signal comprising a nucleic acid comprising a sequence at least 75% identical to the sequence of SEQ ID NO:8.

2. The polyadenylation signal according to claim 1 comprising a sequence at least 80% identical to the sequence of SEQ ID NO:8.

3. The polyadenylation signal according to claim 1 comprising a sequence at least 85%, 90%, 95% or 98% identical to the sequence of SEQ ID NO:8.

4. The polyadenylation signal according to claim 1 comprising the sequence of SEQ ID NO:8.

5. The polyadenylation signal according to claim 1 wherein said polyadenylation signal is operably linked to a heterologous coding sequence.

6. A vector comprising a polyadenylation signal comprising a nucleic acid comprising a sequence at least 75% identical to the sequence of SEQ ID NO:8.

7. The vector of claim 6 comprising a heterologous gene of interest encoding for a heterologous product of interest.

8. The vector of claim 7, wherein the product of interest is a polypeptide of interest and said polypeptide of interest is an antibody, antibody fragment or fusion protein.

9. A cell comprising the vector of claim 6.

10. The cell according to claim 9, wherein said polyadenylation signal is operably linked to a transcription unit encoding a product of interest and wherein the product of interest is a polypeptide of interest encoded by a gene of interest.

11. The cell according to claim 9, wherein said cell is a hamster cell.

12. A method of making a polypeptide of interest encoded by a gene of interest, the method comprising:
    (a) Providing a cell according to claim 10,
    (b) Cultivating said cell, under conditions which allow the proliferation of the cell and the expression of the gene of interest,
    (c) Harvesting the polypeptide of interest and
    (d) Purifying the polypeptide of interest.

13. A kit comprising a polyadenylation signal comprising a nucleic acid comprising a sequence at least 75% identical to the sequence of SEQ ID NO:8, a vector, a cell and a cell culture medium for cultivation of said cell.

14. The vector of claim 6 comprising a sequence at least 80% identical to the sequence of SEQ ID NO:8.

15. The vector of claim 6 comprising a sequence at least 85%, 90%, 95% or 98% identical to the sequence of SEQ ID NO:8.

16. The vector of claim 6 comprising the sequence of SEQ ID NO:8.

17. A vector or polynucleotide sequence comprising (i) a polyadenylation signal comprising a nucleic acid comprising a sequence at least 75% identical to the sequence of SEQ ID NO:8 and (b) a heterologous coding sequence, wherein said polyadenylation signal is operably linked to said heterologous coding sequence.

18. The vector or polynucleotide sequence of claim 17 comprising a sequence at least 80% identical to the sequence of SEQ ID NO:8.

19. The vector or polynucleotide sequence of claim 17 comprising a sequence at least 85%, 90%, 95% or 98% identical to the sequence of SEQ ID NO:8.

20. The vector or polynucleotide sequence of claim 17 comprising the sequence of SEQ ID NO:8.

21. The vector or polynucleotide sequence of claim 17, wherein said heterologous coding sequence comprises a heterologous gene of interest encoding a heterologous product of interest.

22. The vector or polynucleotide sequence of claim 17, wherein the product of interest is a polypeptide of interest and said polypeptide of interest is an antibody, antibody fragment or fusion protein.

23. A cell comprising the vector or polynucleotide sequence of claim 17.

24. The cell according to claim 23, wherein said cell is a hamster cell.

25. The cell according to claim 23, wherein said heterologous coding sequence comprises a heterologous gene of interest encoding a heterologous product of interest, wherein said product of interest is a polypeptide of interest.

26. A method of making a polypeptide of interest encoded by a gene of interest, the method comprising:
    (a) Providing a cell according to claim 23,
    (b) Cultivating said cell, under conditions which allow the proliferation of the cell and the expression of the gene of interest,
    (c) Harvesting the polypeptide of interest and
    (d) Purifying the polypeptide of interest.

* * * * *